(12) United States Patent
Cook et al.

(10) Patent No.: US 7,101,993 B1
(45) Date of Patent: Sep. 5, 2006

(54) OLIGONUCLEOTIDES CONTAINING 2'-O-MODIFIED PURINES

(75) Inventors: Phillip Dan Cook, San Marcos, CA (US); Daniel Peter Claude McGee, Boulder, CA (US); Charles John Guinosso, Visia, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 07/967,267

(22) Filed: Oct. 27, 1992

Related U.S. Application Data

(63) Continuation-in-part of application No. 07/918,362, filed on Jul. 23, 1992, now Pat. No. 5,506,351, which is a continuation-in-part of application No. 07/463,358, filed on Jan. 11, 1990, now abandoned, which is a continuation-in-part of application No. 07/566,977, filed on Aug. 13, 1990, now abandoned.

(51) Int. Cl.
*C07H 21/00* (2006.01)
*C07H 21/04* (2006.01)

(52) U.S. Cl. .................. 536/25.6; 536/22.1; 536/26.1; 536/27.61; 536/27.81; 536/24.5

(58) Field of Classification Search ............... 536/24.5, 536/27.61, 27.81, 25.6, 26.1, 22.1
See application file for complete search history.

(56) References Cited

U.S. PATENT DOCUMENTS

| | | | |
|---|---|---|---|
| 4,511,713 A | 4/1985 | Miller et al. | |
| 5,013,830 A | 5/1991 | Ohtsuka et al. | |
| 5,214,135 A | 5/1993 | Srivastava et al. | ......... 536/26.7 |
| 5,466,786 A | 11/1995 | Buhr et al. | ............... 435/26.26 |
| 5,658,731 A | 8/1997 | Sproat et al. | .................. 435/6 |

FOREIGN PATENT DOCUMENTS

| | | |
|---|---|---|
| CA | 2017369 | 5/1990 |
| DE | 3915462 | 5/1989 |
| DE | 4110085 | 10/1992 |
| DE | 41 10 085 A1 | 10/1992 |
| EP | 0260032 | 3/1988 |
| EP | 0 269 574 A2 | 6/1988 |
| EP | 0399330 | 5/1990 |
| EP | 0378518 | 7/1990 |
| EP | 0519463 | 12/1992 |
| WO | WO 91/06556 | 5/1991 |
| WO | WO 91/15499 | 10/1991 |

OTHER PUBLICATIONS

Chavis, C. et al., "Synthesis of 2', 3'–Differentiated Ribonucleosides via Lycosylation Reactions with 2'–O–TBDMS Ribofuranose Derivatives. A. Pyrimidine Series", *J. Org. Chem.* 1982, 47, 202–206.

Divakar, K.J. et al., "Reaction Between 2,2'–Anhydro–1–β–D–arabinofuranosyluracil and Thiolate Ions", *J. Chem. Soc. Perkin Trans.* 1982, 1625–1628.

Singer, B. and Kusmierek, "Alkylation of Ribose in RNA Reacted with Ethylnitrosourea at Neutrality", *Biochemistry* 1976, 15(23), 5052–5057.

Wagner, D. et al., "Preparation and Synthetic Utility of Some Organotin Derivatives of Nucleosides", *J. Org. Chem.* 1974, 39(1), 24–30.

Chemical Abstracts, vol. 110, Jan. 24, 1989, Abstract No. 24,228; Kikuchi et al., Z. Naturforsch., B: Chem. Sci. 43(5): 623–630, 1988.

Sproat, et al., "2'–O–Alkyloligoribonucleotides: Synthesis and Applications in Studying RNA Splicing", *Nucleosides & Nucleotides*, 1991, 10, 25–35.

Guinosso, et al., "Synthesis and Biophysical and Biological Evaluation of 2'–Modified Antisense Oligonucleotides", *Nucleosides & Nucleotides*, 1991, 10, 259–262.

Inoue, et al., "Sequence–Dependent Hydrolysis of RNA Using Modified Oligonucleotide Splints and RNase H", *FEBS Letters*, 1987, 215, 327–330.

Inoue, et al., "Synthesis and Properties of Novel Nucleic Acid Probes", *Nuc. Acids Res.*, 1985, 16, 165–168.

Cotten et al., *Nucleic Acids Research*, 1991, 19, 2629–2635.
Gladkaya et al., *Khim. Prir. Soedin.*, 1989, 4, 568.
Hansske et al., *Tetrahedron*, 1984, 40, 125–135.
Inoue et al., *Nucleic Acids Research*, 1987, 15, 6131–6148.
Iribarren et al., *Proc. Natl. Acad. Sci.*, 1990, 87, 7747–7751.
Robins et al., *J. Org. Chem.*, 1974, 39, 1891–1899.
Robins et al., *Can. J. Chem.*, 1981 59, 3360–3364.
Singer et al., *Biochemistry* 1976, 15, 5052–5057.
Sproat et al, *Nucleic Acids Research*, 1990, 18, 41–49.
Sproat et al., *Nucleic Acids Research*, 1991, 19, 733–738.
Wagner, et al., *Nucleic Acids Research*, 1991, 19, 5965–5971.
Khurshid et al., *FEBS Letters* 1972, 28:1,25.

(Continued)

*Primary Examiner*—Shaojia A. Jiang
*Assistant Examiner*—Ganapathy Krishnan
(74) *Attorney, Agent, or Firm*—ISIS Patent Department Woodcock Washburn LLP

(57) ABSTRACT

Compounds are provided containing purine nucleotides that bear moieties X at the 2' position thereof wherein X is $R_1$—$(R_2)_n$; $R_1$ is $C_3$–$C_{20}$ alkyl, $C_4$–$C_{20}$ alkenyl or $C_2$–$C_{20}$ alkynyl; $R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides; and n is an integer from 0 to about 6. Such compounds are useful for modulating the synthesis of proteins.

15 Claims, No Drawings

OTHER PUBLICATIONS

Kielanowska et al., *Nucleic Acids Research* 1976, 3:3,817.
Kusmierek et al., *ACTA Biochimica Polonica* 1973, 20:4, 365.
Pike et al., *J. Org. Chem*, 1974. 39:25,3674.
Ransford et al., *J. Carbohydrates—Nucleosides—Nucleotides* 1974, 1:3,275.
Rottman et al., *Biochemistry* 1974, 13,2762.
Tazawa et al., *Biochemistry* 1972, 11,4931.

Robins, et al., "Nucleic acid related compounds. 36. Synthesis of the 2'-O-methyl and 3'-O-methyl ethers of guanosine and 2-aminoaldenosine and correlations of O'-methylnucleoside C nmr spectral shifts", *Can. J. Chem.*, 59, (1981), 3360–3364.

Keller, et al., "A General Method for the Synthesis of 2'-O-Modified Ribonucleosides", *Helvetica Chimica Acta*, 76, (1993), 884–892.

US 7,101,993 B1

OLIGONUCLEOTIDES CONTAINING 2'-O-MODIFIED PURINES

CROSS REFERENCE TO RELATED APPLICATIONS

This application is a continuation-in-part of application Ser. No, 07/918,362, filed on Jul. 23, 1992, now U.S. Pat. No. 5,506,351 which is a continuation-in-part of application Ser. No. 07/463,358 filed on Jan. 11, 1990, now abandoned and application Ser. No. 07/566,977 filed on Aug. 13, 1990 now abandoned. This application is related to application Ser. No. 566,977, filed on Aug. 13, 1990 now abandoned. These applications are assigned to the assignee of the present application and are incorporated by reference herein in their entirety.

BACKGROUND OF THE INVENTION

This invention is directed to novel 2'-O-alkyl guanosine and guanosine analogs and methods of use thereof.

A limited number of oligonucleotide analogs have been made. One class of oligonucleotides that have been synthesized are the 2'-O-substituted oligonucleotides. Such oligonucleotides have certain useful properties. In U.S. patent application Ser. No. 814,961, filed Dec. 24, 1991, entitled Gapped 2' Modified Phosphorothioate Oligonucleotides, assigned to the same assignee as this application, the entire contents of which are herein incorporated by reference, 2' substituted nucleotides are introduced within an oligonucleotide to induce increased binding of the oligonucleotide to a complementary target strand while allowing expression of RNase H activity to destroy the targeted strand. In a recent article, Sproat, B. S., Beijer, B. and Iribarren, A., *Nucleic Acids Research*, 1990, 18, 41 the authors noted further use of 2'-O-methyl substituted oligonucleotides as "valuable antisense probes for studying pre-mRNA splicing and the structure of spliceosomes". 2'-O-methyl and ethyl nucleotides have been reported by a number of authors. Robins, et al., *J. Org. Chem.*, 1974, 39, 1891; Cotten, et al., *Nucleic Acids Research*, 1991, 19, 2629; Singer, et al., *Biochemistry* 1976, 15, 5052; Robins, *Can. J. Chem.* 1981, 59, 3360; Inoue, et al., *Nucleic Acids Research*, 1987, 15, 6131; and Wagner, et al., *Nucleic Acids Research*, 1991, 19, 5965.

A number of groups have taught the preparation of other 2'-O-alkyl guanosine. Gladkaya, et al., *Khim. Prir. Soedin.*, 1989, 4, 568 discloses $N_1$-methyl-2'-O-(tetrahydropyran-2-yl) and 2'-O-methyl guanosine and Hansske, et al., *Tetrahedron*, 1984, 40, 125 discloses a 2'-O-methylthiomethylguanosine. It was produced as a minor by-product of an oxidization step during the conversion of guanosine to 9-β-D-arabinofuranosylguanine, i.e. the arabino analogue of guanosine. The addition of the 2'-O-methylthiomethyl moiety is an artifact from the DMSO solvent utilized during the oxidization procedure. The 2'-O-methylthiomethyl derivative of 2,6-diaminopurine riboside was also reported in the Hansske et al. publication. It was also obtained as an artifact from the DMSO solvent.

Sproat, et al., *Nucleic Acids Research*, 1991, 19, 733 teaches the preparation of 2'-O-allyl-guanosine. Allylation of guanosine required a further synthetic pathway. Iribarren, et al., *Proc. Natl. Acad. Sci.*, 1990, 87, 7747 also studied 2'-O-allyl oligoribonucleotides. Iribarren, et al. incorporated 2'-O-methyl-, 2'-O-allyl-, and 2'-O-dimethylallyl-substituted nucleotides into oligoribonucleotides to study the effect of these RNA analogues on antisense analysis. Iribarren found that 2'-O-allyl containing oligoribonucleotides are resistant to digestion by either RNA or DNA specific nucleases and slightly more resistant to nucleases with dual RNA/DNA specificity, than 2'-O-methyl oligoribonucleotides. However, Iribarren found that 2'-O-dimethylallyl containing oligoribonucleotides exhibited reduced hybridization to complementary RNA sequences as compared to 2'-O-methyl oligoribonucleotides. Thus, Iribarren suggested that further attempts to prepare alkylated RNA probes, especially those superior to 2'-allyl cytidine containing oligoribonucleotides should be limited to 2'-O-alkyl groups containing less than five carbon atoms.

In some cases it is desireable to provide 2'-O-alkyl groups having long chain alkyl groups (i.e. four or more carbon atoms). For example, long chain alkyl groups may accomodate functional groups in appropriate orientation with the opposing strand upon strand hybridization. Thus, 2'-O-long chain alkyl nucleotides such as 2'-O-long chain alkyl guanosine nucleotides are highly desireable in some cases. Novel 2-O-alkylated guanosine compounds are greatly desired. The present invention provides such compounds.

BRIEF DESCRIPTION OF THE INVENTION

Compounds having the structure:

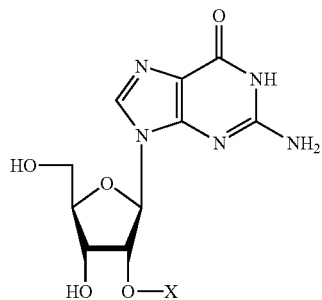

I wherein X is $R_1$—$(R_2)_n$;

$R_1$ is $C_3$–$C_{20}$ alkyl, $C_4$–$C_{20}$ alkenyl or $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides; and n is an integer from 0 to about 6; are provided in some embodiments of the invention. In more preferred embodiments of the present invention n is from 1 to about 3. In still more preferred embodiments of the present invention n is 1.

Preferred compounds of the invention include 2'-O-propylguanosine, 2'-O-pentylguanosine, 2'-O-nonylguanosine, 2'-O-octadecylguanosine, 2'-O-(N-phthalimido)-pentylguanosine, and 2'-O-(imidazol-1-yl) butylguanosine.

In other embodiments of the present invention compounds having the structure:

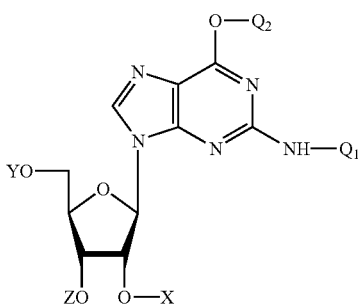

II wherein X is $R_1—(R_2)_n$;

$R_1$ is $C_3$–$C_{20}$ alkyl;

$R_2$ is $NH_2$, H-imidazole or N-phthalimido;

Y is a hydroxyl blocking group;

Z is phosphate or an activated phosphate group;

$Q_1$ and $Q_2$ independently are H or a guanosine blocking group; and n is an integer from 0 to about 6, are provided.

In other aspects of the invention compounds are provided having the structure:

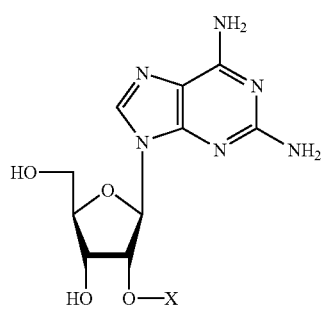

III wherein X is $R_1—(R_2)_n$;

$R_1$ is $C_3$–$C_{20}$ alkyl, $C_4$–$C_{20}$ alkenyl or $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyethylene glycol, polyether, a group that enhances the pharmacodynamic properties of oligonucleotides, or a group that enhances the pharmacokinetic properties of oligonucleotides; and n is an iteger from 0 to about 6.

Compounds of the present invention may be incorporated into oligomers. Thus, in some aspects of the present invention are provided oligomers containing at least one subunit having the structure:

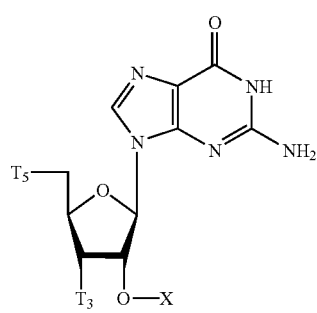

IV wherein X is $R_1—(R_2)_n$;

$R_1$ is $C_3$–$C_{20}$ alkyl, $C_4$–$C_{20}$ alkenyl or $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, and a group that enhances the pharmacokinetic properties of oligonucleotides;

$T_3$ and $T_5$ independently are OH or a further subunit of said oligomer that is joined to said structure; and n is an integer from 0 to about 6.

In other aspects of the invention, are provided oligomers containing at least one subunit having the structure:

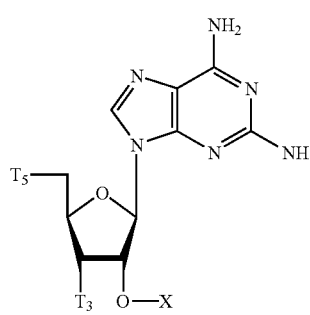

V wherein X is $R_1—(R_2)_n$;

$R_1$ is $C_1$–$C_{20}$ alkyl, $C_2$–$C_{20}$ alkenyl or $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, and a group that enhances the pharmacokinetic properties of oligonucleotides; $T_3$ and $T_5$ independently are OH or a further subunit of said oligomer that is joined to said structure; and n is an integer from 0 to about 6.

Methods of modulating the synthesis of a protein are also provided by the present invention comprising specifically hybridizing with mRNA coding for said protein an oligomer containing at least one subunit having the structure:

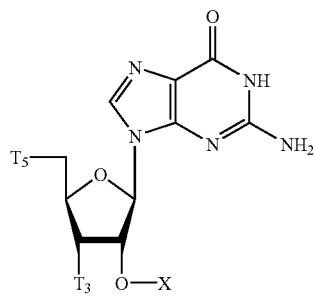

wherein X is $R_1-(R_2)_n$;

$R_1$ is $C_3-C_{20}$ alkyl, $C_4-C_{20}$ alkenyl or $C_2-C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl,.NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides; $T_3$ and $T_5$ independently are OH or a further subunit of said oligomer that is joined to said structure; and n is an integer from 0 to about 6.

In still other aspects of the invention methods of modulating the synthesis of a protein are provided comprising specifically hybridizing with mRNA coding for said protein an oligomer containing at least one subunit having the structure:

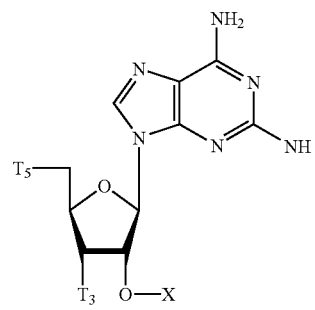

wherein X is $R_1-(R_2)_n$;

$R_1$ is $C_1-C_{20}$ alkyl, $C_2-C_{20}$ alkenyl or $C_2-C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides; $T_3$ and $T_5$ independently are OH or a further subunit of said oligomer that is joined to said structure; and n is an integer from 0 to about 6.

DETAILED DESCRIPTION OF THE INVENTION

This invention includes compounds having the structure:

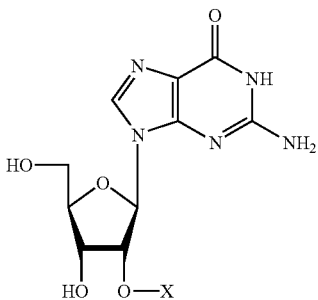

I wherein X is $R_1-(R_2)_n$;

$R_1$ is $C_3-C_{20}$ alkyl, $C_4-C_{20}$ alkenyl or $C_2-C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides; and n is an integer from 0 to about 6.

In other embodiments of the present invention compounds having the structure:

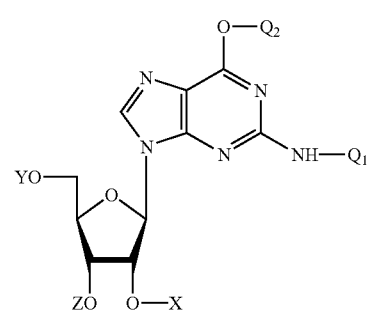

II wherein X is $R_1-(R_2)_n$;

$R_1$ is $C_3-C_{20}$ alkyl;

$R_2$ is $NH_2$, H-imidazole, N-phthalimido;

Y is a hydroxyl blocking group;

Z is phosphate or an activated phosphate group;

$Q_1$ and $Q_2$ independently are H or a guanosine blocking group; and n is an integer from 0 to about 6, are also provided.

In still other embodiments of the present invention compounds having the structure:

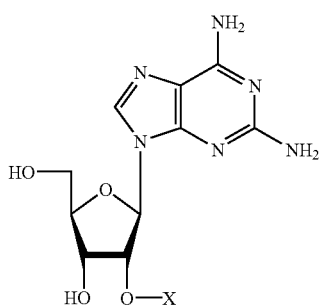

III wherein X is $R_1$—$(R_2)_n$;

$R_1$ is $C_3$–$C_{20}$ alkyl, $C_4$–$C_{20}$ alkenyl or $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, and a group that enhances the pharmacokinetic properties of oligonucleotides; and n is an integer from 0 to about 6, are provided.

Compounds of Formulas I, II and III may be prepared by alkylation effected directly on 2,6-diamino-9-(β-D-ribofuranosyl)purine with an appropriate compound having the formula $R_1$—L, wherein $R_1$ is $C_3$–$C_{20}$ alkyl, $C_4$–$C_{20}$ alkenyl or $C_2$–$C_{20}$ alkynyl and L is a leaving group, in the presence of a base of sufficient strength to effect removal of the proton from the 2' or 3' (or both 2' and 3') hydroxyl of the ribofuranosyl sugar moiety of 2,6-diamino-9-(β-D-ribofuranosyl)purine. When used in the general sense, the term "alkyl" or "alkylation" is meant to refer to herein to alkyl, alkenyl and alkynyl groups. Alkyl, alkenyl and alkynyl groups of the present invention may be straight chain, branched or cyclic groups.

In more preferred embodiments of the present invention $R_1$ is $C_4$–$C_{20}$ alkyl and in still more preferred embodiments of the present invention $R_1$ is $C_5$ to $C_{20}$ alkyl. Alkylation can be limited to mono alkylation by limiting the amount of either the $R_1$—L group or the base to a stoichiometric (or equivalent) amount. Alternately dialkylation (on both the 2' and 3' positions) can be practiced by use of an excess $R_1$—L group and base to concurrently alkylate both the 2' and the 3' positions.

It has been observed that alkylation predominates at the 2' position compared to the 3' position. Generally a ratio of from about 7:3 to about 8:2 of 2' to 3' alkylation products are obtained (as determined by TLC). For both TLC as well as preparative scale chromatography, the 2' product generally has a faster Rf than the 3' product. Advantage can be taken of this Rf difference to separate the 2'-O- and 3'-O-products from each other or from 2'-O-,3'-O-dialkylated products. Thus the 2' and 3' alkylation products can be separated by procedures such as silica gel chromatography if desired.

For alkyl groups that are generally larger than propyl, further advantage can be taken of the rate of deamination of the 2' product versus the 3' product for separation of the 2'-O and 3'-O products. Thus mixtures of 2'-O and 3'-O alkylated 2,6-diamino-9-(β-D-ribofuranosyl)-purine are subjected to deamination with adenosine deaminase. The enzymatic deamination of the 2'-O product is more facile than deamination of the 3'-O product. This difference in the rate of deamination allows for separation of the deaminated 2' product, i.e. the 2'-O-alkylated guanosine, from the slower or non-deaminated 3' product, i.e. the 2,6-diamino-9-(3'-O-alkylated-β-D-ribofuranosyl)purine. Additionally procedures such as crystallization has been utilized to further separate a 2' product from the corresponding 3' product by separating the 2'-O-alkylated diaminopurine riboside product from the corresponding 3'-O-alkylated diaminopurine riboside product.

A preferred base utilized for alkylation is sodium hydride. Other suitable bases may also be utilized, however such bases must have sufficient base strength to remove the proton from the 2' (or 3') hydroxyl moiety of the 2,6-diamino-purine riboside starting material. While not wishing to be bound by theory, generally any base having a $pK_a$ about 10 $pk_a$ units greater than the $pK_a$ of the proton of the 2' hydroxyl moiety of the 2,6-diaminopurine riboside starting material may be used. More specifically, bases having a $pK_b$ greater than the $pK_b$ of sodium hydride may conveniently be selected. Such bases can be selected from compilations of base such as those given in Table 1, page 220 of March, J. *Advanced Organic Chemistry*, Wiley-Interscience, John Wiley & Sons, New York, 1985.

The alkylation reactions useful to prepare compounds of the invention typically are conducted in DMF as the solvent. Other suitable solvents include DMSO, N-methyl pyrolidone and sulfolone.

Preferably, deamination is effected by use of deaminase enzymes. Particularly preferred is adenosine deaminase. Particularly suitable for use is Adenosine Deaminase Type II available from Sigma Chemical Company, St. Louis, Mo. Other deamination reagents may also be employed. The deamination reactions of the invention typically are conducted in a mixture solvent containing an organic solvent and an aqueous buffer. Suitable for use as the organic solvent are DMSO, N-methyl pyrolidone and sulfolone. In preferred embodiments of the present invention deamination is achieved using DMSO as the organic solvent. Suitable for use as the aqueous buffer are buffers having a pH compatible to the pH range of use of the deaminase enzyme. Preferred are phosphate buffers such as sodium phosphate and tris buffers.

In order to enrich the 2' product verse 3' product by elimination of any 3' product, a TIPDS (tetraisopropylsiloxane) protecting group is utilized to protect the 3' and 5' hydroxyl moieties of the sugar portions of the 2,6-diaminopurine riboside. In the same manner, exclusive 3' product would be obtainable by use of a base stable, non-migratory 2'-O-protecting group. Such base stable, non-migratory protecting groups include but are not limited to tetrahydropyranyl (THP), 4-methoxytetrahydropyran-4-yl (Mthp), 1-[(2-chloro-4-methyl)phenyl-4-methoxypiperidin-4-yl (Ctmp), triphenylmethyl (trityl), mono-, di- and trimethoxytrityl and other similar protecting groups.

Suitable leaving groups of the present invention include halides such as chloride, bromide, and iodide, sulfonates such as tosyl, brosyl, nosyl, mesyl and trifyl and oxonium ions. In preferred embodiments of the present invention the leaving group is a halide. Still other suitable leaving groups are well known to those skilled in the art.

The 3'-O-phosphoramidite of 2'-O-alkyl guanosine and 2,6-diamino-9-(2'-O-alkyl-β-D-ribofuranosyl)purine are provided in the present invention by reaction of $2NH_2$, 5'-OH protected 2'-O-alkyl guanosine or $2NH_2$, $6NH_2$, and 5'-OH protected 2,6-diamino-9-(2'-O-alkyl-β-D- ribofuranosyl)purine with a reagent such as 2-cyanoethyl N,N-diisopropylamino-chlorophosphine. 2'-O-alkyl guanosine and 2'-O-alkyl-2,6-diaminopurine riboside are phosphitylated at the 3'-OH to provide phosphoramidites. In conducting such phosphitylation the NHz moieties (2NHz or 2NH$_2$ and 6NH$_2$, respectively) are protected. Next the 5'-OH moiety is protected followed by reaction with cyanoethyl N,N-diisopropylaminochlorophosphine.

Compounds of the present invention can be incorporated into oligomers by procedures known to those skilled in the art. Oligomers of the present invention may contain at least one subunit having the structure:

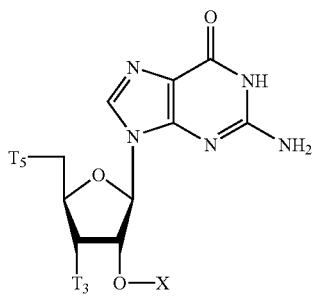

wherein X is $R_1$—$(R_2)_n$;

$R_1$ is $C_3$–$C_{20}$ alkyl, $C_4$–$C_{20}$ alkenyl $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

$T_3$ and $T_5$ independently are OH or a further nucleotide or nucleoside of said oligonucleotide or oligonucleoside that is joined to said structure; and n is an integer from 0 to about 6.

In still other embodiments of the present invention oligomers may contain at least one subunit having the structure:

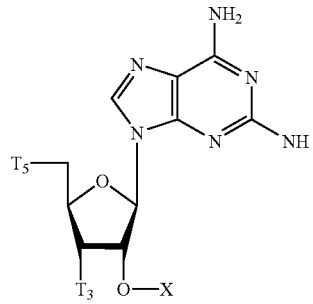

wherein X is $R_1$—$(R_2)_n$;

$R_1$ is $C_1$–$C_{20}$ alkyl, $C_2$–$C_{20}$ alkenyl $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

$T_3$ and $T_5$ independently are OH or a further nucleotide or nucleoside of said oligonucleotide or oligonucleoside that is joined to said structure; and n is an integer from 0 to about 6.

Such oligomers or oligonucleotides may be prepared by solid state synthesis or by other means known to those skilled in the art. For example, 2'-O-alkyl guanosine phosphoramidites and derivatives thereof may be incorporated into oligonucleotides using standard phosphoramidite chemistry. Incorporation of 2'-O-alkyl guanosine nucleotides will confer desireable characteristics to an oligonucleotide such as enhanced resistance to nuclease.

In the context of this invention, the term "oligonucleotide" or "oligomer" refers to a polynucleotide formed from naturally occuring bases and furanosyl groups joined by native phosphodiester bonds. Oligonucleotides of the present invention will, of course, comprise at least one 2'-O-alkyl guanosine or derivative thereof. Thus, this term effectively refers to naturally occurring species or synthetic species formed from naturally occurring subunits or their close homologs. The term "oligonucleotide" or "oligomer" may also refer to moieties which have portions similar to naturally occurring oligonucleotides but which have non-naturally occurring portions. Thus, oligonucleotides may have altered sugars, altered base moieties, or altered inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the messenger RNA is located. It is preferred that such substitutions comprise phosphorothioate bonds, phosphotriesters, methyl phosphonate bonds, short chain alkyl or cycloalkyl structures or short chain heteroatomic or heterocyclic structures. Other preferred substitutions are CH$_2$—NH—O—CH$_2$, CH$_2$—N(CH$_3$)—O—CH$_2$, CH$_2$—O—N(CH$_3$)—CH$_2$, CH$_2$—N(CH$_3$)—N(CH$_3$)—CH$_2$ and O—N(CH$_3$)—CH$_2$—CH$_2$ structures where phosphodiester intersugar linkage is replaced by the substitutions. Also preferred are morpholino structures. Summerton, J. E. and Weller, D. D., U.S. Pat. No. 5,034,506 issued Jul. 23, 1991. In other preferred embodiments, such as the protein-nucleic acid (PNA) backbone, the phosphodiester backbone of the oligonucleotide may be replace with a polyamide backbone, the bases being bound directly or indirectly to the aza nitrogen atoms of the polyamide backbone. P. E. Nielsen, et al., *Science* 1991 254 1497. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Suitable bases include, but are not limited to those described in U.S. Pat. No. 3,687,808. similarly, modifications on the furanosyl portion of the nucleotide subunits, in addition to 2'-O-alkyl modifications of the present invention, may also be effected, as long as the essential tenets of this invention are adhered to. Examples of such modifications are 2'-halogen-substituted nucleotides. Some specific examples of modifications at the 2' position of sugar moieties which are useful in the present invention are OH, SH, SCH$_3$, F, OCN, O(CH$_2$)$_n$NH$_2$, Cl, Br, CN, CF$_3$, OCF$_3$, S— or N— alkyl; S— or N-alkenyl; SOCH$_3$, SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively function as subunits in the oligonucleotide.

Preferably oligonucleotides of the present invention are from about 6 to about 50 nucleotides in length. In still more preferred embodiments of the present invention oligonucleotides are from about 12 to about 20 nucleotides in length.

Intercalators are molecules which insert themselves between neighboring bases of an oligonucleotide. A well known intercalator is acridine. Other intercalators will be apparent to one skilled in the art. Reporter molecules are molecules which may aid in the identification of a molecule, either visually or otherwise. For example, biotin and various fluorophores are effective reporter groups. Conjugates, or bifunctional linkers effectively join two groups. Some conjugates are commercially available such as biotin or 3' maleimidobenzoyl-N-hydroxy-succinimide available from Boehringer Mannheim (Indianapolis, Indiana). Pharmacodymanic property improvement means, in this context, improved oligonucleotide uptake, enhanced oligonucleotide resistance to degradation, and/or strengthened sequence-specific hybridization with RNA. Such groups do not initiate chemical reactions. Groups that enhance the pharmacodynamic properties of an oligonucleotide preferrably include alkyl chains, polyamines, ethylene glycols, polyamides, alkyl chains, aminoalkyl chains and amphipathic moieties. Pharmacokinetic property improvement means improved oligonucleotide uptake, distribution, metabolism or excretion.

Antisense therapy involves the use of oligonucleotides which are specifically hybridizable to target RNA or DNA. Oligonucleotides of the present invention are preferably specifically hydridizable with a target region. By "specifically hybridizable" herein is meant capable of forming a stable duplex with a target DNA or RNA. Upon binding to, or forming a stable duplex with, the target RNA or DNA, the antisense oligonucleotide can selectively inhibit the genetic expression of these nucleic acids or can induce some other events such as destruction of a targeted RNA or DNA or activation of gene expression. Destruction of targeted RNA can be effected by RNase H activation or by linking strand cleavers to the oligonucleotide. Antisense therapy is known in the art. See for example, PCT/US91/05720 filed Dec. 3, 1991 entitled "Antisense Oligonucleotide Inhibitors of Papillomavirus" and PCT/US91/01327 filed Feb. 25, 1991 entitled "Oligonucleotide Therapies for Modulating the Effects of Herpesvirus".

In some embodiments of the present invention the oligonucleotide portions of compounds of the present invention are at least 60% complementary to a target sequence. In preferred embodiments of the present invention the oligonucleotide portions of compounds of the present invention are at least 80% complementary to a target sequence. 100% complementarity of the oligonucleotide portions of compounds of the present invention to a target sequence is most preferred. In preferred embodiments of the present invention, the oligonucleotide portions may be specifically hybridizable with DNA or RNA from Candida, papilloma virus, Epstein Barr virus, rhinovirus, hepatitis, human immunodeficiency virus, herpes simplex virus, influenza virus and cytomegalovirus.

2-O-alkyl guanosine containing oligonucleotides of the present invention may be used to modulate the production of protein by contacting a selected sequence of RNA or DNA coding for a selected protein with an 2'-O-alkyl guanosine containing oligonucleotide of the present invention having a sequence of nucleotide bases specifically hybridizable with said selected sequence of RNA or DNA coding for said protein.

The oligonucleotides of the present invention can be used in diagnostics, therapeutics and as research reagents. For therapeutic use, an animal having a disease characterized by the undesired production of a protein is contacted with an oligonucleotide of the present invention having a sequence of nucleotide bases specifically hybridizable with a selected sequence of RNA or DNA coding for said protein.

EXAMPLES

The following examples illustrate the invention, however, they are not intended as being limiting.

Example 1

2,6-Diamino-9-(β-D-ribofuranosyl)purine

In accordance with modifications of the procedures described in Robins, M. J., Hanske, F. and Beriner, S. E., Can. J. Chem., 59:3360 (1981), guanosine hydrate (49 g, Aldrich Chemical Co.), toluene (200 ml), hexamethyldisilazane (160 ml, 4.3 eq) and trifluoromethanesulfonic acid (3.7 ml) were loaded in a stainless steel Parr bomb. The bomb was sealed and heated approximately ⅓ submerged in an oil bath at 170° C. for 5 days. The bomb was cooled in a dry ice acetone bath and opened. The contents were transferred to a 2 liter round bottom flask using methanol (MeOH) and the solvent evaporated on a Buchii evaporator. 1:1 H$_2$O/MeOH (600 ml) was added to the residue and the resulting brown suspension was refluxed 4–5 hr. The resulting suspension was evaporated on the Buchii evaporator to remove the methanol (≈½volume). Additional H$_2$O (≈300 ml) was added and the mixture was heated, treated with charcoal and filtered through a Celite filter pad. Upon cooling, a crystalline solid formed. The solid was isolated by filtration, washed with H$_2$O and dried under high vacuum at 90° C. to yield the product (43.7 g, 89% yield) as a tan solid. UV and NMR spectra of this compound compared to literature values.

This variation of the procedures of Robins, et al. supra, eliminated the need to utilize liquid ammonia in the reaction mixture since the ammonia molecule is generation in situ from the silazane reagent and the water of hydration of the guanosine hydrate starting material. Further, the use of chlorotrimethylsilane was not necessary nor was it necessary to conduct the reaction under anhydrous conditions, do a preliminary evaportaion, or open and re-seal the Parr bomb under a dry nitrogen atmosphere.

Example 2

2,6-Diamino-9-(2-O-propyl-β-D-ribofuranosyl) purine & 2,6-Diamino-9-(3-O-propyl-β-D-ribofuranosyl)purine Sodium hydride (NaH) (2.1 g) was added to 2,6-diamino-9-(β-D-ribofuranosyl)purine (10.5 g) in dry dimethylformamide (DMF) (150 ml). After stirring for 10 min, iodo-propane (6 ml) was added. The solution was stirred for 45 min at room temperature followed by the addition of a further aliquot of NaH (600 mg). The reaction mixture was stirred overnight and then quenched by the addition of ethanol (EtOH) (5 ml). The reaction mixture was evaporated in vacuo, the residue suspended in 10% MeOH/$CH_2CL_2$ and purified by silica gel chromatography (300 g) using 5→10% MeOH/$CH_2Cl_2$ as the eluent. The 2',3'-di-O-propyl product eluted first followed by the 2'-O-propyl product and then the 3'-O-propyl product. The 2'-O-propyl product containing fractions were pooled and the solvent stripped to yield a crude foam. The foam was crystallized from $H_2O$ (40 ml), washed with cold $H_2O$ and dried to yield 2.9 g of the 2'-O-propyl compound. The mother liquor was evaporated, re-chromatographed and crystallized to yield an additional 2.4 g of the 2'-O-propyl compound. The second mother liquor was evaporated to yield 4 g of a mixture of 2' and 3'-O-propyl compounds as an oil. Fractions containing the 3'-O-propyl product as the major product were evaporated and residue foam crystallized from water. (See Example 17 below for isolation and characterization of the 2',3'-di-O-propyl compound).

2,6-Diamino-9-(2-O-propyl-β-D-ribofuranosyl) purine $^1$H NMR (DMSO-$d_6$) δ 0.76 (t, 3, C$\underline{H}_3$), 1.4 (tq, 2, C$\underline{H}_2$), 3.3 (m, 1, $\underline{H}$-5"+HDO), 3.65–3.45 (m, 3, $\underline{H}$-5', O—C$\underline{H}_2$), 3.9 (m, 1), 4.25 (br m, 1), 4.38 (dd, 1), 5.1 (br d, 1 3'-O$\underline{H}$), 5.45 (br t, 1, 5'-OH), 5.75 (br s, 2, 6-N$\underline{H}_2$), 5.83 (d, 1, $\underline{H}$-1'), 6.77 (br s, 2, 2-N$\underline{H}_2$) and 7.95 (s, 1, $\underline{H}$-8). Anal. Calcd. for $C_{13}H_{20}N_6O_4 \cdot \frac{1}{2}H_2O$: C, 46.91; H, 6.2; N, 25.25. Found: C, 47.09; H, 6.37; N, 25.33.

2,6-Diamino-9-(3-O-propyl-βB-D-ribofuranosyl) purine $^1$H NMR (DMSO-$d_6$) δ 0.75 (t, 3, C$\underline{H}_3$), 1.4 (tq, 2, C$\underline{H}_2$), 3.27–3.5 (ABX 2, O—C$\underline{H}_2$—), 3.5 and 3.6 (ABX, 2, $\underline{H}$-5'), 3.9 (m, 1), 4.22 (m, 1), 4.35 (m, 1), 5.1 (br d, 1, 2'-O$\underline{H}$), 5.45 (br t, 1, 5'-O$\underline{H}$), 5.75 (br s, 2, 6-N$\underline{H}_2$), 5.8 (d, 1, $\underline{H}$-1'), 6.8 (br s, 2, 2-$\underline{H}_2$) and 7.95 (s, 1, $\underline{H}$-8).

Example 3

2'-O-Propylguanosine

A mixture of 2,6-Diamino-9-(2'-O-propyl-β-D-ribofuranosyl)purine and 2,6-Diamino-9-(3'-O-propyl-β-D-ribofuranosyl)purine (4.6 gm) and adenosine deaminase (200 mg, Sigma Chemicals Type II) were stirred at room temperature overnight in 0.1 M tris buffer (150 ml, pH 7.4), DMSO (100 ml) and 0.1 M sodium phosphate buffer (10 ml). A further aliquot of adenosine deaminase (140 mg) in 0.1 M phosphate buffer (30 ml) and DMSO (20 ml) was added and the reaction stirred an addition 24 hrs. The solvent was evaporated in vacuo and the residue flash chromatographed on silica gel utilizing 5→20% MeOH/$CH_2Cl_2$. Product-containing fractions were evaporated in vacuo and the residue crystallized from $H_2O$ to yield 2.6 gm of product. m.p. dec>270° C. $^1$H NMR (DMSO-$d_6$) δ 0.75 (t, 3, C$\underline{H}_3$), 1.42 (tq, 2, C$\underline{H}_2$), 3.3–3.6 (m, 4, $\underline{H}$-5', O—C$\underline{H}_2$), 3,85 (m, 1), 4.2 (m, 1), 4.23 (m, 1), 5.10 (t, 1, 5'-O$\underline{H}$), 5.13 (d, 1, 3'-O$\underline{H}$), 5.75 (d, 1, $\underline{H}$-1'), 6.45 (br s, 2, N$\underline{H}_2$), 7.95 (s, 1, $\underline{H}$-8) and 10.67 (br s, 1, N$\underline{H}$). Anal. Calcd. for $C_{13}H_{19}N_5O_5$: C, 47.99; H, 5.89; N, 21.53. Found: C, 47.90, H, 5.85; N, 21.44.

Example 4

N2-Isobutyryl-2'-O-propylguanosine

2'-O-Propylguanosine (3.6 gm) in pyridine (50 ml) was cooled in an ice bath and trimethylsilyl chloride (8.4 ml, 6 eq.) was added. The reaction mixture was stirred for 30 min and isobutyryl chloride (5.8 ml, 5 eq.) was added. The solution was stirred for 4 hours during which it was allowed to warm to room temperature. The solution was cooled, $H_2O$ added (10 ml) and the solution was stirred for an additional 30 mins. Concentrated $NH_4OH$ (10 ml) was added and the solution evaporated in vacuo. The residue was purified by silica gel chromatography using 10% MeOH/$CH_2CL_2$ to elute the product. Product-containing fractions were evaporated to yield 2.5 g of product as a foam. An analytical sample was re-chromatographed on silica and eluted with $CH_2Cl_2$→6% MeOH/$CH_2Cl_2$. $^1$H NMR (DMSO-$d_6$) δ 0.75 (t, 3, C$\underline{H}_3$), 1.13 [d, 6, CH(C$\underline{H}_3$)$_2$], 1.4 (m, 2, C$\underline{H}_2$), 2.75 [m, 1, C$\underline{H}$(CH$_3$)$_2$], 3.52 (m, 6, OC$\underline{H}_2$), 3.36 and 3.6 (ABX, 2, $\underline{H}$-5'), 3.95 (m, 1), 4.26 (m, 1), 4.33 (m, 1), 5.07 (t, 1, 5'-O$\underline{H}$), 5.18 (d, 1, 3'-O$\underline{H}$), 5.9 (d, 1, $\underline{H}$-1'), 8.25 (s, 1, $\underline{H}$-8), 11.65 (br s, 1, N$\underline{H}$) and 12.1 (br s, 1, N$\underline{H}$). Anal. Calcd. for $C_{17}H_{25}N_5O_6 \cdot \frac{1}{2}H_2O$: C, 50.49; H, 6.48; N, 17.32. Found: C, 50.81; H, 6.62; N, 17.04.

Example 5

N2-Isobutyryl-5'-dimethoxytrityl-2'-O-propylguanosine

N2-Isobutyryl-2'-O-propylguanosine (2.64 g) was co-evaporated with pyridine and then solubilized in pyridine (180 ml). Dimethoxytrityl chloride (2.4 g, 1.1 eq) and dimethylaminopyridine (50mg) was added with stirring at room temperature. The reaction mixture was stirred overnight and evaporated in vacuo. The residue was partitioned between $CH_2Cl_2$/2×dil $Na_2CO_3$. The organic phase was dried ($MgSO_4$) and evaporated. The residue was purified by silica gel chromatography (1:1 EtOAc/Hex→5% MeOH/EtOAc, 1% TEA) to yield 4.1 g of product. $^1$H NMR (DMSO-$d_6$) δ 0.78 (t, 3, C$\underline{H}_3$), 1.12 [d, 6, CH(C$\underline{H}_3$)$_2$], 1.46 (m, 2, C$\underline{H}_2$), 2.75 [m, 1, C$\underline{H}$(CH$_3$)$_2$], 3.35 and 3.55 (ABX, 2, $\underline{H}$-5'), 3.73 (s, 6, OC$\underline{H}_2$), 4.0 (m, 1), 4.3 (m, 1), 4.4 (m, 1), 5.18 (d, 1, 3'-O$\underline{H}$), 5.93 (d, 1, $\underline{H}$-1'), 6.8, 7.2, 7.36 (m, 13, DMTr), 8.13 (s, 1, $\underline{H}$-8), 11.63 (br s, 1, N$\underline{H}$) and 12.1 (br s, 1, N$\underline{H}$). Anal. Calcd. for $C_{38}H_{42}N_5O_8 \cdot H_2O$: C, 63.83; H, 6.20; N, 9.80. Found: C, 64.22; H, 6.35; N, 9.55.

Example 6

N2-Isobutyryl-5'-dimethoxytrityl-2'-O-propylguanosine 3'-β-cyanoethyl-N,N-diisopropylphosphoramidate A $CH_2Cl_2$ solution of N2-Isobutyryl-5'-dimethoxytrityl-2'-O-propylguanosine (4.1 g), bis-(N,N-diisopropylamino)-2-cyanoethylphosphite (3.7 ml, 2 eq) and N,N- diisopropylammonium tetrazolide (0.5 g, 0.5 eq) was stirred at room temperature overnight. The solution was partitioned against dil. Na$_2$CO$_3$ and then dil. Na$_2$CO$_3$/NaCl and dried over MgSO$_4$. The solvent was evaporated in vacuo and the residue was purified by silica gel chromatography (120 g, 1% TEA in EtOAc) to yield 5.2 g of product as a foam. $^{31}$P NMR (CDCl$_3$) δ 150.5, 150.8.

Example 7

2,6-Diamino-9-(2-O-pentyl-β-D-ribofuranosyl) purine & 2,6-Diamino-9-(3-O-pentyl-β-D-ribofuranosyl)purine 2,6-Diamino-9-(β-D-ribofuranosyl)purine (10 g) was treated with sodium hydride (1.7 g, 1.2 eq) and bromopentane (5.3 ml, 1.2 eq) in DMF (90 ml) as per the procedure of Example 2. Silica gel chromatography yielded three components. The first eluted component (not characterized but believed to be the 2,3-di-(O-pentyl) compound was isolated as an oil (700 mg). The next component isolated as a foam (3.3 g) was crystallized from MeOH to yield of 2.8 g of 2,6-diamino-9-(2-O-pentyl-β-D-ribofuranosyl)purine. The third component isolated as a solid (200 mg) was crystallized from MeOH to yield 80 mg of 2,6-diamino-9-(3-O-pentyl-β-D-ribofuranosyl)purine. Fractions containing mixtures of the first and second components were evaporated and the residue crystallized from MeOH to yield a further 900 mg of the 2-O-pentyl compound. Further fraction yielded 1.2 g of a mixture of the 2'-O-pentyl and 3'-O-pentyl compounds.

2,6-Diamino-9-(2-O-pentyl-β-D-ribofuranosyl) purine $^1$H NMR (DMSO-d$_6$) δ 0.75 (t, 3, CH$_3$), 1.16 (m, 4, CH$_2$), 1.39 (m, 2, CH$_2$), 3.53 (m, 2, CH$_2$), 3.3 and 3.6 (ABX, 2, H-5'), 3.93 (br s, 1), 4.23 (m, 1), 4.38 (m, 1), 5.1 (d, 1 3'-OH), 5.5 (t, 1, 5'-OH), 5.75 (br s, 2, 6-NH$_2$), 5.82 (d, 1, H-1'), 6.8 (br s, 2, 2-NH$_2$) and 7.93 (s, 1, H-8).

2,6-Diamino-9-(3-O-pentyl-β-D-ribofuranosyl) purine $^1$H NMR (DMSO-d$_6$) δ 0.87 (t, 3, CH$_3$), 1.3 (m, 4, CH$_2$), 1.55 (m, 2, CH$_2$), 3.5 (m, 2, O—CH$_2$—), 3.6 (m, 2, H-5'), 3.86 (m, 1), 3.95 (m, 1), 4.6 (m, 1), 5.32 (br d, 1 2'-OH), 5.46 (br t, 1, 5'-OH), 5.70 (d, 1, H-1'), 5.75 (br s, 2, 6-NH$_2$), 6.76 (br s, 2, 2-NH$_2$) and 7.93 (s, 1, H-8).

Example 8

2'-O-Pentylguanosine 2,6-diamino-9-(2-O-pentyl-β-D-ribofuranosyl)purine (1.9 g) in 0.1 M sodium phosphate buffer (50 ml, pH 6.0) and DMSO (25 ml) was treated with adenosine deaminase (added in two aliquots—first aliquot 50 mg, second aliquot 80 mg) at 35° C. as per the procedure of Example 3 to yield 1.4 g of product. $^1$H NMR (DMSO-d$_6$) δ 0.8 (t, 3, CH$_3$), 1.16 (m, 4, 2×CH$_2$), 1.4 (m, 2, CH$_2$), 3.38, 3.6 (m, 4, OCH$_2$, H-5'), 3.93 (s, 1, H-4'), 4.28 (m, 2, H-2', H-3'), 5.17 (br, 2, 5', 3'-OH), 5.8 (d, 1, H-1'), 6.53 (br s, 2, NH$_2$), 8.0 (s, 1, H-8) and 10.68 (br, 1, NH)).

Example 9

N2-Isobutyryl-2'-O-pentylguanosine

2'-O-pentylguanosine (2.3 g) in pyridine (35 ml) was treated with trimethylsilyl chloride (4.15 ml, 5 eq) and isobutyryl chloride (3.4 ml, 5 eq) as per the procedure of Example 4 to yield the product as a foam (2.3 g). An analytical sample was crystallized from EtOAc/Hex. m.p. 178–180° C. $^1$H NMR (DMSO-d$_6$) δ 0.75 (t, 3, CH$_3$), 1.1 [m, 10, 2×CH$_2$, CH(CH$_3$)$_2$], 1.4 (m, 2, CH$_2$), 2.74 [m, 1, CH(CH$_3$)$_2$], 3.56 (m, 4, OCH$_2$, H-5'), 3.93 (m, 1, H-4'), 4.25 (m, 1), 4.34 (m, 1), 5.05 (t, 1, 5'-OH), 5.17 (d, 1, 3'-OH), 5.88 (d, 1, H-1'), 8.27 (s, 1, H-8), 11.65 (br s, 1, NH) and 12.05 (br s, 1, NH). Anal. Calcd. for C$_{19}$H$_{29}$N$_5$O$_6$: C, 53.89; H, 6.90; N, 16.54. Found: 53.75; H, 6.92; N, 16.40

Example 10

N2-Isobutyryl-5'-dimethoxytrityl-2'-O-pentylguanosine

N2-Isobutyryl-2'-O-pentylguanosine (2.3 g) was treated with dimethoxytrityl chloride (1.7 g, 1.1 eq), and dimethylaminopyridine (100 mg as a catalyst) in pyridine (50 ml) as per the procedure of Example 5 to yield the product as a foam (2.9 g). $^1$H NMR (DMSO-d$_6$) δ 0.83 (t, 3, CH$_3$), 1.2 [m, 10, 2×CH$_2$, CH(CH$_3$)$_2$], 1.48 (m, 2, CH$_2$), 2.78 [m, 1, CH(CH$_3$)$_2$], 3.4, 3.6 (m, 4, OCH2, H-5'), 3.75 (s, 6, OCH$_3$), 4.07 (m, 1), 4.27 (m, 1), 4.42 (m, 1), 5.2 (br d, 1, 3'-OH), 5.95 (d, 1, H-1'), 6.85, 7.25, 7.38 (m, 13, DMTr), 8.15 (s, 1, H-8), 11.67 (br s, 1, NH) and 12.1 (br s, 1, NH). Anal. Calcd. for Anal. Calcd. for C$_{40}$H$_{47}$N$_5$O$_8$.½H$_2$O: C, 65.38; H, 6.58; N, 9.53. Found: C, 65.37; H, 6.59; N, 9.39.

Example 11

N2-Isobutyryl-5'-dimethoxytrityl-2'-O-pentylguanosine 3'-β-Cyanoethyl-N,N-diisopropylphosphoramidate N2-Isobutyryl-5'-dimethoxytrityl-2'-O-pentyl-guanosine (1.7 g) was treated with bis-(N,N-diisopropylamino)-2-cyanoethyl-phosphite (1.48 g) and N,N-diisopropylammonium tetrazolide (200 mg) as per the procedure of Example 6 to yield the product (1.4 g). $^{31}$P NMR (CDCl$_3$) δ 150.5, 150.85.

Example 12

2,6-Diamino-9-(2-O-nonyl-β-D-ribofuranosyl)purine 2,6-Diamino-9-(β-D-ribofuranosyl)purine (50 g, 180 mmol) was treated with sodium hydride (8.8 g, 220 mmol) and bromononane (59 g, 54.4 ml, 285 mmol) in DMF (700 ml) as per the procedure of Example 2 (the diamino compound in DMF was cooled in an ice bath during the addition of NaH) to yield 83 g of crude product. 50 g of crude product was purified by silica gel chromatography. Fraction containing 2'-O-nonyl and 3'-O-nonyl product were combined to give a 77:23 mixture (29 g) of the 2' and 3' product. Pure 2'-O-nonyl product is obtained by chromatography. $^1$H NMR (DMSO-d$_6$) δ 0.95 (t, 3, CH$_3$); 1.17 [m, 12, O—CH$_2$—CH$_2$—(CH$_2$)$_6$; 1.42 [m, 2, O—CH$_2$CH$_2$(CH$_2$)$_6$]; 3.27–3.70 (m, 2, H-5'); 3.50–3.70 [m, 2, O—CH$_2$(CH$_2$)$_7$]; 3.95 (m, 1, H-4'), 4.24 (m, 1, H-3'); 4.40 (m, 1, H-2'); 5.10 (d, 1, 3'-OH, J=5 Hz); 5.50 (t, 1, 5'-OH, J=6 Hz); 5.76 (s, 2, 2-NH$_2$); 5.83 (d, 1, H-1', J=6.0 Hz); 6.81 (s, 2, 6-NH$_2$); and 7.96 (s, 1, 8-H).

Example 13

2'-O-Nonylguanosine

A mixture of 2,6-diamino-9-(2-O-nonyl-β-D-ribofuranosyl)purine and 2,6-diamino-9-(3-O-nonyl-β-D- ribofuranosyl)purine (≈80:20 mixture, 29 g) in 0.1 M sodium phosphate buffer (50 ml, pH 7.4), 0.1 M tris buffer (1800 ml, pH 7.4) and DMSO (1080 ml) was treated with adenosine deaminase (1.6 g) as per the procedure of Example 3 to yield 60 g of product as an oil. An analytical product was purified by silica gel chromatography and recrystallized from EtOAc. m.p. 258–259° C. $^1$H NMR (DMSO-$d_6$) δ 0.96 (t, 3, C$\underline{H}_3$, J=7 Hz); 1.17 [m, 12, O—CH$_2$—CH$_2$—(C$\underline{H}_2$)$_6$]; 1.42 [m, 2, O—CH$_2$C $\underline{H}_2$(CH$_2$)$_6$]; 3.27–3.61 (m, 4, $\underline{H}$-5', O—C$\underline{H}_2$(CH$_2$)$_7$]; 3.95 (m, 1, $\underline{H}$-4'), 4.10–4.13 (m, 2, $\underline{H}$-2', $\underline{H}$-3'); 5.13–6.06 (m, 2, 3'-O$\underline{H}$5'-O$\underline{H}$); 5.80 (d, 1, $\underline{H}$-1', J=6.4 Hz); 6.47 (s, 2, 2-N$\underline{H}_2$); 7.98 (s, 1, 8-$\underline{H}$) and 10.64 (s, 1, N$_1$ amide). Anal. Calcd. for C$_{19}$H$_{31}$N$_5$O$_5$: C, 55.73; H, 7.63; N, 17.10. Found: C, 55.67; H, 7.66; N, 17.02.

Example 14

N2-Isobutyryl-2'-O-nonylguanosine

2'-O-nonylguanosine (14.7 g) in pyridine (360 ml) was treated with trimethylsilyl chloride (23.4 ml) and isobutyryl chloride (30.6 ml) as per the procedure of Example 4 to yield crude product (37 g). The crude material was purified by silica gel chromatography (eluted with 90/10 CHCl$_3$/MeOH) to yield 14.6 g of product re-crystallized from EtOAc. m.p. 168–169° C. $^1$H NMR (DMSO-$d_6$) δ 0.85 [t, 3, C$\underline{H}_3$(nonyl)], 1.14 [m, 18, O—CH$_2$CH$_2$(C$\underline{H}_2$)$_6$, CH(C$\underline{H}_3$)$_2$], 1.40 [m, 2, O—CH$_2$C$\underline{H}_2$(CH$_2$)$_6$], 2.79 [m, 1, C$\underline{H}$(CH$_3$)$_2$], 3.31–3.63 (m, 4, $\underline{H}$-5', O—C$\underline{H}_2$(CH$_2$)$_7$]; 3.96 (m, 1, $\underline{H}$-4'), 4.27–4.37 (m, 2, $\underline{H}$-2', $\underline{H}$-3'); 5.10 (t, 1, 5'-O$\underline{H}$, J=5 Hz), 5.18 (d, 1, 3'-O$\underline{H}$, J=4 Hz), 5.91 (d, 1, $\underline{H}$-1', J=6.6 Hz), 8.31 (s, 1, 8-$\underline{H}$), 11.73 (s, 1, C2 amide) and 12.11 (s, 1, N$_1$ amide). Anal. Calcd. for C$_{23}$H$_{37}$N$_5$O$_6$: C, 57.60; H, 7.78; N, 14.60. Found: C, 57.63; H, 7.92; N, 14.62.

Example 15

N2-Isobutyryl-5'-dimethoxytrityl-2'-O-nonylguanosine

N2-Isobutyryl-2'-O-nonylguanosine (14.6 g, 30.4 mmol) was treated with dimethoxytrityl chloride (12.1 g, 34 mmol) in pyridine (200 ml) as per the procedure of Example 5 to yield 16 g of purple foam prior to chromatography and 11.5 g after chromatography purification. $^1$H NMR (DMSO-$d_6$) δ 0.84 [t, 3, C$\underline{H}_3$(nonyl), J=7 Hz], 1.16 [m, 18, O—CH$_2$CH$_2$(C$\underline{H}_2$)$_6$, CH(C$\underline{H}_3$)$_2$], 1.43 [m, 2, O—CH$_2$C$\underline{H}_2$(CH$_2$)$_6$], 2.77 [m, 1, C$\underline{H}$(CH$_3$)$_2$], 3.18–3.63 (m, 4, $\underline{H}$-5', O—C$\underline{H}_2$(CH$_2$)$_7$]; 3.74 (s, 6, DMTr O—C$\underline{H}_3$) 4.06 (m, 1, $\underline{H}$-4'), 4.27 (m, 1, $\underline{H}$-3'); 4.42 (m, 1, $\underline{H}$-2'); 5.19 (d, 1, 3'-O$\underline{H}$, J=5 Hz), 5.94 (d, 1, $\underline{H}$-1', J=5.7 Hz), 6.83–7.38 (m, 13, DMTr aromatic), 8.14 (s, 1, 8-$\underline{H}$), 11.65 (s, 1, C$_2$ amide) and 12.11 (s, 1, N$_1$ amide). Anal. Calcd. for C$_{44}$H$_{55}$N$_5$O$_8$: C, 67.59; H, 7.27; N, 8.96. Found: C, 67.59; H, 7.11; N, 8.80.

Example 16

N2-Isobutyryl-5'-dimethoxytrityl-2'-O-nonylguanosine 3'-β-cyanoethyl-N,N-diisopropylphosphoramidate N2-Isobutyryl-5'-dimethoxytrityl-2'-O-nonylguanosine (2.1 g) was treated with bis-(N,N-diisopropylamino)-2-cyanoethyl-phosphine (1.5 g) and N,N-diisopropylammonium tetrazolide (0.2 g) as per the procedure of Example 6 to yield the product (2.0 g). $^{31}$P NMR (CDCl$_2$) δ 150.7 and 150.4 (diastereomers).

Example 17

2,6-Diamino-9-(2,3-di-O-propyl-β-D-ribofuranosyl]purine

The procedure of Example 2 was repeated utilizing 2,6-diamino-9-(β-D-ribofuranosyl)purine (10 g), NaH (3 g) and 1-bromo-propane (10 ml) in DMF. After evaporation of the reaction solvent, the reaction products were purified by silica gel chromatography. The slower moving component yielded 4.3 g of the 2'-O-propyl product as a foam. This foam was crystallized from water to yield 3.6 g of product. The faster moving component isolated as an oil formed crystals upon standing. EtOH was added to the crystals, they were filtered and wash 1×EtOH to yield 1.1 grams of 2', 3'-di-O-propyl product. m.p. 165–167° C. $^1$H NMR (DMSO-$d_6$) δ 0.80 and 0.92 (t, 6, C$\underline{H}_3$), 1.6 and 1.45 (m, 4, C$\underline{H}_2$), 3.7–3.45 (br m, 6), 4.07 (m, 2), 4.5 (dd, 1), 5.55 (br t, 1, 5'-O$\underline{H}$), 5.8 (br s, 2, 6-N$\underline{H}_2$), 5.85 (d, 1, $\underline{H}$-1'), 6.84 (br s, 2, 2-N$\underline{H}_2$) and 8.0 (s, 1, $\underline{H}$-8).

Anal. Calcd. for C$_{16}$H$_{26}$N$_6$O$_4$: C, 52.45; H, 7.15; N, 22.94. Found: C, 52.18; H, 7.19; N, 22.75.

Example 18

N2,N6-Diisobutyryl-2,6-diamino-9-(2-O-propyl-β-D-ribo-furanosyl)purine 2,6-diamino-9-(2-O-propyl-β-D-ribofuranosyl)purine (2.0 g) in pyridine (35 ml) was treated with trimethylsilyl chloride (3.9 ml, 5 eq) and isobutyryl chloride (3.2 ml, 5 eq) as per the procedure of Example 4 to yield a foam after silica gel chromatography. The foam was crystallized from EtOAc/Hex to yield 2.2 g of product. m.p. 140–142° C. $^1$H NMR (DMSO-$d_6$) δ 0.77 (t, 3, C$\underline{H}_3$), 1.07, 1.16 [d, 12, 2×CH(C$\underline{H}_3$)$_2$], 1.5 (m, 2, C$\underline{H}_2$), 2.9, 3.03 [m, 2, 2×C$\underline{H}$(CH$_3$)$_2$], 3.4 (m, 1, $\underline{H}$-5''), 3.58 (m, 3, OC$\underline{H}_2$, $\underline{H}$-5'), 3.95 (m, 1, $\underline{H}$-4'), 4.3 (m, 1), 4.5 (m, 1), 5.02 (t, 1, 5'-O$\underline{H}$), 5.2 (d, 1, 3'-O$\underline{H}$), 6.03 (d, 1, $\underline{H}$-1'), 8.58 (s, 1, $\underline{H}$-8), 10.39 (br s, 1, N$\underline{H}$), and 10.57 (br s, 1, N$\underline{H}$).

Example 19

N2,N6-Diisobutyryl-2,6-diamino-9-(5-O-dimethoxytrityl-2-O-propyl-β-D-ribofuranosyl)purine N2,N6-Diisobutyryl-2,6-diamino-9-(2-O-propyl-β-D-ribo-furanosyl)purine (1.9 g) was treated with dimethoxytrityl chloride (1.5 g, 1.1 eq), and dimethylaminopyridine (20 mg as a catalyst) in pyridine (50 ml) as per the procedure of Example 5 to yield the product as a foam (2.8 g). $^1$H NMR (DMSO-$d_6$) δ 0.79 (t, 3, C$\underline{H}_3$), 1.07, 1.16 [d, 12, 2×CH(C$\underline{H}_3$)$_2$], 1.5 (m, 2, C$\underline{H}_2$), 2.9, 3.03 [m, 2, 2×C$\underline{H}$(CH$_3$)$_2$], 3.58 (m, 3, OC$\underline{H}_2$, $\underline{H}$-5'), 4.15 (m, 1, $\underline{H}$-4'), 4.4 (m, 1), 4.6 (m, 1), 5.15 (d, 1, 3'-O$\underline{H}$), 6.15 (d, 1, $\underline{H}$-1'), 6.8–7.35 (m, 13, DMTr), 8.5 (s, 1, $\underline{H}$-8), 10.3 (br s, 1, N$\underline{H}$), and 10.57 (br s, 1, N$\underline{H}$).

Example 20

N2,N6-Diisobutyryl-2,6-diamino-9-(5-O-dimethoxytrityl-2-O-propyl-β-D-ribofuranosyl) purine 3'-β-Cyanoethyl-N,N-diisopropylphosphoramidate N2,N6-Diisobutyryl-2,6-diamino-9-(5-O-dimethoxytrityl-2-O-propyl-β-D-ribofuranosyl)purine (2.6g) was treated with bis-(N,N-diisopropylamino)-2-cyanoethylphosphite (1.7 g) and N,N-diisopropylammonium tetrazolide (300 mg) overnight at room temperature. The reaction mixture was partitioned against dil. Na$_2$CO$_3$/CHCl$_2$ and then Na$_2$CO$_3$/NaCl and dried over MgSO$_4$. The organic layer was evaporated to a foam. The foam was dissolved in CH$_2$Cl2 (≈8 ml) and slowly added to Hexanes (500 ml). The solid was filtered and dried to yield the product as a powder (3.1 g). $^{31}$P NMR (CDCl$_3$) δ 150.8 and 151.3.

Example 21

2,6-Diamino-9-[2-O-(N-phthalimido)propyl-β-D-ribofuranosyl]purine & 2,6-Diamino-9-[3-O-(N-phthalimido)propyl-β-D-ribofuranosyl]purine 2,6-Diamino-9-(β-D-ribofuranosyl)purine (14.2 g) was treated with sodium hydride (3 g, 1.5 eq) and N-(3-bromopropyl) phthalimide (5.3 ml, 1.5 eq) in DMF (200 mL) at 70° C. overnight. The reaction mixture was proportioned between $H_2O$ and Hexanes (1×), then extracted 4×$CH_2Cl_2$. The organic layer was dried over $MgSO_4$ and evaporated to a residue. The residue was purified by silica gel chromatography eluted with MeOH/$CH_2Cl_2$. The 2'-O-(N-phthalimido)propyl product eluted first followed by mixed fractions and then the 3'-O-(N-phthalimido) product. Evaporations of the fractions gave 3.4 g of the 2'-O-(N-phthalimido)propyl product, 3.0 g of mixed 2' and 3' products and 1.4 g of the 3'-O-(N-phthalimido)propyl product all as foams. The 3'-O-(N-phthalimido)propyl product was crystallized from EtOAc/MeOH to give 270 mg of solid.

2,6-Diamino-9-[2-O-(N-phthalimido)propyl-β-D-ribofuranosyl]purine $^1$H NMR (DMSO-$d_6$) δ 1.8 (tq, 2, —C$\underline{H}_2$—), 3.4–3.58 (m, 6, 2×C$\underline{H}_2$, $\underline{H}$-5'), 3.9 (m, 1), 4.26 (m, 1), 4.37 (m, 1), 5.05 (br d, 1, 3'-O$\underline{H}$), 5.4 (br t, 1, 5'-O$\underline{H}$), 5.72 (br s, 2, N$\underline{H}_2$), 5.8 (br d, 1, $\underline{H}$-1'), 6.75 (br s, 2, N$\underline{H}_2$), 7.8 (br s, 4, Ar) and 8.93 (s, 1, $\underline{H}$-8).

2,6-Diamino-9-[3-O-(N-phthalimido)propyl-β-D-ribofuranosyl]purine m.p. 220–222° C., $^1$H NMR (DMSO-$d_6$) δ 1.85 (tq, 2, —C$\underline{H}$—N), 3.6–3.67 (m, 4, —O—C$\underline{H}_2$, $\underline{H}$-5'), 3.85 (m, 1), 3.92 (m, 1), 4.6 (m, 1), 5.33 (d, 1, 2'-O$\underline{H}$), 5.45 (br t, 1, 5'-O$\underline{H}$), 5.65 (d, 1, $\underline{H}$-1'), 5.73 (br s, 2, N$\underline{H}_2$), 6.75 (br d, 2, N$\underline{H}_2$), 7.8–7.85 (m, 4, Ar) and 7.85 (s, 1, $\underline{H}$-8). Anal. Calcd. for $C_{21}H_{23}N_7O_6$: C, 53.73; H, 4.94; N, 20.88. Found: C, 53.59; H, 4.89; N, 20.63.

Example 22

2'-O-(N-Phthalimido)propylguanosine 2,6-diamino-9-[2-O-(N-phthalimido)propyl-β-D-ribofuranosyl] purine (3.1 g) in 0.1 M sodium phosphate buffer (3 ml, pH 7.4), 0.05 M tris buffer (65 ml, pH 7.4) and DMSO (45 ml) was treated with adenosine deaminase (200 mg) at room temperature for 5 days as per the procedure of Example 3. The product containing fractions from the silica gel chromatography were evaporated and upon concentration formed white crystals. The crystals were filtered and washed with MeOH to yield 1.1 g of product. An analytical sample was recrystallized from MeOH. m.p. 192–194° C. $^1$H NMR (DMSO-$d_6$) δ 1.82 (m, 2, C$\underline{H}_2$), 3.45–3.67 (m, 6, $\underline{H}$-5', OC$H_2$, NC$\underline{H}_2$), 3.9 (m, 1), 4.3 (m, 2, $\underline{H}$-2', $\underline{H}$-3'), 5.1 (m, 2, 5' and 3'-OH), 5.8 (d, 1, $\underline{H}$-1'), 6.5 (br s, 2, N$\underline{H}_2$), 7.83 (s, 4, phthal), 7.98 (s, 1, $\underline{H}$-8) and 10.5 (br s, 1, N$\underline{H}$). Anal. Calcd. for $C_{21}H_{22}N_6O_7 \cdot \frac{1}{2}H_2O$: C, 52.61; H, 4.83; N, 17.53. Found: C, 52.52; H, 4.78; N, 17.38.

Example 23

N2-Isobutyryl-2'-O-(N-phthalimido)propylguanosine

2'-O-(N-phthalimido)propylguanosine (7.2 g, crude) in pyridine (35 ml) was treated with trimethylsilyl chloride (11.6 ml, 5 eq) and isobutyryl chloride (8 ml, 5 eq) as per the procedure of Example 4 to yield the product as a crude foam (6.5 g). An analytical sample was obtained by crystallization from EtOAc. m.p. 166–168° C. $^1$H NMR (DMSO-$d_6$) δ 1.15 [d, 6, —CH(C$\underline{H}_3$)$_2$], 1.85 (m, 2, C$\underline{H}_2$), 2.8 [m, 1, C$\underline{H}$(CH$_3$)$_2$], 3.45–3.7 (m, 6, H-5', OC$\underline{H}_2$, NC$\underline{H}_2$), 3.95 (m, 1), 4.34 (m, 1), 4.4 (m, 1), 5.12 (t, 1, 5'-O$\underline{H}$), 5.18 (d, 1, 3'-O$\underline{H}$), 5.9 (d, 1, $\underline{H}$-1'), 7.83 (s, 4, phthal), 8.3 (s, 1, $\underline{H}$-8), 11.65 (br s, 1, N$\underline{H}$) and 12.1 (br s, 1, N$\underline{H}$). Anal. Calcd. for $C_{25}H_{28}N_6O_8 \cdot \frac{1}{2}H_2O$: C, 54.64; H, 5.32; N, 15.29. Found: C, 54.46; H, 5.39; N, 14.98.

Example 24

N2-Isobutyryl-5'-dimethoxytrityl-2'-O-(N-phthalimido)propylquanosine

N2-Isobutyryl-2'-O-(N-phthalimido)propylguanosine (1.2 g) was treated with dimethoxytrityl chloride (820 mg, 1.1 eq), and dimethylaminopyridine (20 mg as a catalyst) in pyridine (50 ml) as per the procedure of Example 5 utilizing 1:1 Hex/EtOAc, then EtOAc then 5%MeOH/EtOAc with 1% TEA as eluent. The product containing fraction were evaporated to yield the product as a foam (1.7 g). $^1$H NMR (DMSO-$d_6$) δ 1.1 [d, 6, —CH($\underline{H}_3$)$_2$], 1.85 (m, 2, C$\underline{H}_2$), 2.75 [m, 1, C$\underline{H}$(CH$_3$)$_2$], 3.45–3.7 (m, 6, H-5', OC$\underline{H}_2$, NC$\underline{H}_2$), 3.75 (s, 6, OC$\underline{H}_3$), 4.0 (m, 1), 4.32 (m, 1), 4.4 (m, 1), 5.2 (d, 1, 3'-O$\underline{H}$), 5.93 (d, 1, $\underline{H}$-1'), 6.83, 7.2, 7.35 (m, 13, DMTr), 7.78 (s, 4, phthal), 8.15 (s, 1, $\underline{H}$-8), 11.6 (br s, 1, N$\underline{H}$) and 12.05 (br s, 1, N$\underline{H}$). Anal. Calcd. for $C_{46}H_{46}N_6O_{10} \cdot H_2O$: C, 64.18; H, 5.62; N, 9.76. Found: C, 64.42; H, 5.78; N, 9.53.

Example 25

N2-Isobutyryl-5'-dimethoxytrityl-2'-O-(N-phthalimido)propylguanosine 3'-β-cyanoethyl-N,N-diisopropylphosphoramidate N2-Isobutyryl-5'-dimethoxytrityl-2'-O-(N-phthalimido)propylguanosine (1.6 g) was treated with bis-(N,N-diisopropylamino)-2-cyanoethylphosphite (1.48 g) and N,N-diisopropylammonium tetrazolide (200 mg) as per the procedure of Example 6 to yield the product (2.0 g). $^{31}$P NMR (CDCl$_3$) δ 150.9.

Example 26

N2-Dimethylaminomethylidene-5═-dimethoxytrityl-2'-O-(N-phthal-imido)propylguanosine 2'-O-(N-phthalimido)propylguanosine (900 mg) in DMF (20 ml) was treated with N,N-dimethylformamide dimethyl acetal (2 ml). The reaction mixture was stirred for 2 hr and evaporated under high vac at 52° C. The residue was co-evaporated 1×with pyridine and taken up in solution in pyridine. Dimethoxytrityl chloride (713 mg, 1.1 eq) and dimethylaminopyridine (20 mg as a catalyst) were added. The reaction mixture was stirred overnight, partitioned between Na$_2$CO$_3$/CH$_2$Cl$_2$, dried over MgSO$_4$ and purified by silica gel chromatography as per the procedure of Example 5 to yield 1.7 g of product as an off white solid. $^1$H NMR (DMSO-$d_6$) δ 1.88 (m, 2, C$\underline{H}_2$), 3.1 [d, 6, N=CHN(C$\underline{H}_3$)$_2$], 3.3 (m, 2, $\underline{H}$-5'), 3.67 (m, 4, OC$\underline{H}_2$, NC$_2$), 3.78 (s, 6, 2×OC$\underline{H}_3$), 4.0 (m, 1, $\underline{H}$-4'), 4.35 (m, 2, $\underline{H}$-2', $\underline{H}$-3'), 5.2 (d, 1, 3'-O$\underline{H}$), 5.95 (d, 1, $\underline{H}$-1'), 6.85, 7.25, 7.39 (m, 13, DMTr), 7.85 (s, 4, phthal), 7.95 [s, 1, $\underline{H}$-8), 8.5 (s, 1, N=C$\underline{H}$N(CH$_3$)$_2$] and 11.39 (s, 1, N$\underline{H}_2$). Anal. Calcd. for $C_{45}H_{45}N_7O_9 \cdot \frac{1}{2}H_2O$: C, 64.58; H, 5.54; N, 11.71. Found: C, 64.10; H, 5.65; N, 11.47.

Example 27

N2-Dimethylaminomethylidene-5'-dimethoxytrityl-2'-O-(N-phthalimido)propylguanosine 3'-β-cyanoethyl-N,N-diisopropylphosphoramidate N2-Isobutyryl-5'-dimethoxytrityl-2'-O-(N-phthalimido) propylguanosine (1.7 g), bis-(N,N-diisopropylamino)-2-cyanoethylphosphite (1.4 ml) and N,N-diisopropylammonium tetrazolide (170 mg) were stirred overnight at room temperature. The reaction mixture was partitioned between $CH_2Cl_2$ and $Na_2CO_3$ 2 ×. The organic phase was dried over $MgSO_4$ and evaporated to an oil. The oil was dissolved in a minimum of $CH_2Cl_2$ and added dropwise to ≈900 ml Hexanes to precipitate the product. The solid was isolated and dried to yield 2.1 g of product. $^1P$ NMR ($CDCl_3$) δ 150.4, 150.6.

Example 28

2,6-Diamino-9-[2-O-(N-phthalimido)pentyl-β-D-ribofuranosyl]purine 2,6-Diamino-(9-β-D-ribofuranosyl)purine (6.7 g) was treated with sodium hydride (1.3 g) and N-(3-bromopentyl) phthalimide (7.8 g, 1.1 eq) in DMF (60 ml) at room temperature for three days. The reaction mixture was proportioned between $H_2O$ and $CH_2Cl_2$ and extracted 4×$CH_2Cl_2$. The combined organic layers were dried over $MgSO_4$ and evaporated to a residue. The residue was purified by silica gel chromatography eluted with 5→10% MeOH/$CH_2Cl_2$. The 2'-O-(N-phthalimido)pentyl containing fractions were collected and evaporated to a yellow foam to give 2.2 g of product. An analytical sample was crystallized from EtOH. m.p. 173–175° C. $^1H$ NMR (DMSO-$d_6$) δ 1.2 (m, 2, —C$\underline{H}_2$—), 1.47 (m, 4, 2×C$\underline{H}_2$), 3.55, 3.65 (m, 6, O—C$\underline{H}_2$, $\underline{H}$-5', NC$\underline{H}_2$), 3.95 (m, 1), 4.28 (m, 1), 4.4 (m, 1), 5.13 (d, 1, 3'-O$\underline{H}$), 5.5 (t, 1, 5'-O$\underline{H}$), 5.77 (br s, 2, 6-N$\underline{H}_2$), 5.84 (br d, 1, $\underline{H}$-1'), 6.8 (br s, 2, 2-N$\underline{H}_2$), 7.86 (M, 4, phthal) and 7.95 (s, 1, $\underline{H}$-8). Anal. Calcd. for $C_{23}H_{27}N_7O_6$: C, 55.50; H, 5.47; N, 19.71. Found: C, 55.44; H, 5.51; N, 19.30.

Example 29

2'-O-(N-Phthalimido)pentylguanosine

A mixture of the 2,6-diamino-9-[2-O-(N-phthalimido) pentyl-β-D-ribofuranosyl]purine and 2,6-diamino-9-[3-O-(N-phthalimido) pentyl-β-D-ribofuranosyl]purine isomers (2.2 g) in 0.1 M tris buffer (60 ml, pH 7.4), 0.1 M $NaPO_4$ buffer (2 ml, pH 7.4) and DMSO (40 ml) was treated with adenosine deaminase (60 mg) at room temperature for 5 days as per the procedure of Example 3. The product containing fractions from the silica gel chromatography were evaporated to give the product (1.0 g) as a crude white solid. An analytical sample was prepared by the addition of MeOH to form crystals. m.p. 178–180° C. $^1H$ NMR (DMSO-$d_6$) δ 1.24 (m, 2, C$\underline{H}_2$), 1.5 (m, 4, 2×C$\underline{H}_2$), 3.5–3.6 (m, 6, $\underline{H}$-5', OC$\underline{H}_2$, NC$\underline{H}_2$), 3.87 (m, 1, $\underline{H}$-4'), 4.25 (m, 2, $\underline{H}$-2', $\underline{H}$-3'), 5.1 (m, 2, 5' and 3'-O$\underline{H}$), 5.78 (d, 1, $\underline{H}$-1'), 6.5 (br s, 2, N$\underline{H}_2$), 7.84 (M, 4, phthal), 7.98 (s, 1, $\underline{H}$-8) and 10.67 (br s, 1, N$\underline{H}$). Anal. Calcd. for $C_{23}H_{26}N_6O_7$·½$H_2O$: C, 54.43; H, 5.36; N, 16.56. Found: C, 54.79; H, 5.24; N, 16.61.

Example 30

N2-Isobutyryl-2'-O-(N-phthalimido)pentylguanosine

2'-O-(N-phthalimido)pentylguanosine (1.6 g, crude) in pyridine (35 ml) was treated with trimethylsilyl chloride (2.0 ml, 5 eq) and isobutyryl chloride (1.68 ml, 5 eq) as per the procedure of Example 4 to yield the product as a foam. This foam was co-evaporated 2×with EtOAc followed by the addition of EtOAc and heating to yield white crystals (950 mg). m.p. 202–204° C. $^1H$ NMR (DMSO-$d_6$) δ 1.1 [d, 6, —CH(C$\underline{H}_3)_2$], 1.17 (m, 2, C$\underline{H}_2$), 1.43 (m, 4, 2×C$\underline{H}_2$), 2.74 [m, 1, C$\underline{H}$(CH$_3)_2$], 3.45–3.55 (m, 6, H-5', OC$\underline{H}_2$, NC$\underline{H}_2$), 3.9 (m, 1), 4.25 (m, 1), 4.3 (m, 1), 5.07 (t, 1, 5'-O$\underline{H}$), 5.15 (d, 1, 3'-O$\underline{H}$), 5.87 (d, 1, $\underline{H}$-1'), 7.8 (s, 4, phthal), 8.27 (s, 1, $\underline{H}$-8) 11.67 (br s, 1, N$\underline{H}$) and 12.06 (br s, 1, N$\underline{H}$). Anal. Calcd. for $C_{27}H_{32}N_6O_8$·½$H_2O$: C, 56.14; H, 5.76; N, 14.55. Found: C, 56.45; H, 5.74; N, 14.41.

Example 31

N2-Isobutyryl-5'-dimethoxytrityl-2'-O-(N-phthalimido)pentylguanosine

N2-Isobutyryl-2'-O-(N-phthalimido) pentylguanosine (0.95 g) was treated with dimethoxytrityl chloride (620 mg, 1.1 eq), and dimethylaminopyridine (20 mg as a catalyst) in pyridine (50 ml) as per the procedure of Example 5 utilizing EtOAc 1% TEA and then 5% MeOH EtOAc/$CH_2Cl_2$ with 1% TEA as eluent. The product containing fractions were evaporated to yield the product as a foam (1.4 g). $^1H$ NMR (DMSO-$d_6$) δ 1.14 [d, 6, —CH(C$\underline{H}_3)_2$], 1.25 (m, 2, C$\underline{H}_2$), 1.53 (m, 4, 2×C$\underline{H}_2$), 2.77 [m, 1, C$\underline{H}$(CH$_3)_2$], 3.3–3.6 (m, 6, H-5', OC$\underline{H}_2$, NC$\underline{H}_2$), 3.75 (s, 6, OC$\underline{H}_3$), 4.07 (m, 1), 4.33 (m, 1), 4.4 (m, 1), 5.18 (d, 1, 3'-O$\underline{H}$), 5.94 (d, 1, $\underline{H}$-1'), 6.83, 7.2, 7.53 (m, 13, DMTr), 7.8 (s, 4, phthal), 8.15 (s, 1, $\underline{H}$-8), 11.6 (br s, 1, N$\underline{H}$) and 12.1 (br s, 1, N$\underline{H}$). Anal. Calcd. for $C_{48}H_5ON_6O_{10}$·½$H_2O$: C, 65.52; H, 5.84; N, 9.55. Found: C, 65.55; H, 5.94; N, 9.20.

Example 32

2,6-Diamino-9-[3,5-O-(tetraisopropyldisiloxane-1,3-diyl)-β-D-ribofuranosyl]purine To a suspension of 2,6-diamino-9-(β-D-ribo-furanosyl) purine (10.5 g) in pyridine (100 ml) was added 1,3-dichlorotetraisopropyldisiloxane (TIPDS, 12.6 g). The reaction was stirred at room temperature for 4 hours and an additional 1.3 g of 1,3-dichlorotetraisopropyldisiloxane was added followed by stirring overnight. The reaction mixture was poured into ice water and the insoluble product (11.6 g) collected by filtration. An analytical sample was recrystallized from EtOAc/Hexanes. m.p. 170–172° C. Anal. Calcd. for $C_{22}H_{40}N_6O_5Si_2$·½$H_2O$: C, 49.5; H, 7.74; N, 15.7. Found: 49.57; H, 7.82; N, 15.59.

Example 33

2,6-Diamino-9-[3,5-O-(tetraisopropyldisiloxane-1,3-diyl)-2-O-methyl-β-D-ribofuranosyl]purine A mixture of 2,6-Diamino-9-[3,5-O-(tetraisopropyl-disiloxane-1,3-diyl)-β-D-ribofuranosyl]purine (8.8 g) in DMF (120 ml) and methyl iodide (3 ml, 3 eq) was cooled in an ice bath and NaH (60% in oil, 1.0 g, 1.5 eq) added. After 20 min the reaction was quenched with MeOH and partitioned between sat. $NH_4Cl$ and $CH_2Cl_2$. The organic phase was washed with 1×$NH_4Cl$, dried over $MgSO_4$ and evaporated. The residue was crystallized from hot EtOH/$H_2O$ to yield the product (8.5 g) as crystals. m.p. 87–89° C. $^1H$ NMR (DMSO-$d_6$) δ 1.05 (m, 28, TIPDS), 3.57 (s, 3, OC$\underline{H}$3), 3.98 (m, 1, $\underline{H}$-4'), 3.92 and 4.07 (ABX, 2, $\underline{H}$-5'), 4.13 (d, 1), 4.6 (dd, 1, $\underline{H}$-3'), 5.76 (br s, 2, N$\underline{H}_2$), 5.8 (s, 1, $\underline{H}$-1'), 6.77 (br s, 2, N$\underline{H}_2$) AND 7.77 (s, 1 $\underline{H}$-8).

Example 34

2,6-Diamino-9-(2-O-methyl-β-D-ribofuranosyl) purine

To a solution of 2,6-Diamino-9-[3,5-O-(tetraisopropyldisiloxane-1,3-diyl)-2-O-methyl-β-D-ribofuranosyl] purine (8.5 g) in THF (50 ml) was added 1M tetrabutylammonium fluoride in THF (Aldrich, 20 ml). The reaction mixture was stirred for 2 hrs and filtered. The filter cake was washed with 2×EtOAc and air dried to give 4.0 g of crude product. An analytical sample was crystallized from hot MeOH. m.p. 133–135° C. $^1$H NMR (DMSO-$d_6$) δ 3.3 (s, 3, OC$\underline{H}_3$), 3.58 (m, 2, $\underline{H}$-5'), 3.98 (m, 1, $\underline{H}$-4'), 4.28 (m, 2, $\underline{H}$-2', $\underline{H}$-3'), 5.23 (br s, 1, 3'-O$\underline{H}$), 5.48 (br t, 1, 5'-O$\underline{H}$), 5.77 (br s, 2, N$\underline{H}_2$), 5.82 (d, 1, $\underline{H}$-1'), 6.83 (br s, 2, N$\underline{H}_2$) and 7.95 (s, 1, $\underline{H}$-8). Anal. Calcd. for $C_{11}H_{16}N_6O_4 \cdot \frac{1}{2}H_2O$: C, 43.28; H, 5.61; N, 27.52. Found: C, 43.51; H, 5.62; N, 27.26.

Example 35

2'-O-Methylguanosine 2,6-Diamino-9-(2-O-methyl-β-D-ribofuranosyl)purine (9.5 g) in 0.1 M sodium phosphate buffer (200 ml, pH 7.4) and DMSO (25 ml) was treated with adenosine deaminase (Type II Sigma) at RT for 4 days. The resulting suspension was cooled and filtered and the resulting filter cake washed with $H_2O$ and dried to a white solid (4.0 g). The solid was recrystallized from hot $H_2O$ to yield 2.9 g of product. m.p. 236–238° C. $^1$H NMR (DMSO-$d_6$) δ 3.3 (s, 3, OC$\underline{H}_3$), 3.53 and 3.6 (ABX, 2, $\underline{H}$-5'), 3.87 (m, 1, $\underline{H}$-4'), 4.15 (m, 1, $\underline{H}$-2'), 4.25 (m, 1, $\underline{H}$-3'), 5.13 (t, 1, 5'-O$\underline{H}$), 5.23 (d, 1, 3'-O$\underline{H}$), 5.8 (d, 1, $\underline{H}$-1'), 6.48 (br s, 2, N$\underline{H}_2$), 7.96 (s, 1, $\underline{H}$-8) and 10.68 (br s, 1, N$\underline{H}$). Anal. Calcd. for $C_{11}H_{15}N_5O_5 \cdot \frac{1}{2}H_2O$: C, 43.14; H, 5.26; N, 22.86. Found: C, 43.59; H, 5.34; N, 23.04.

Example 36

N2-Isobutyryl-2'-O-methylguanosine

2'-O-methylguanosine (3.5 g) in pyridine (100 ml) was treated with trimethylsilyl chloride (9 ml, 6 eq) and isobutyryl chloride (6.2 ml) at RT for 4 hr. The reaction mixture was cooled in an ice bath, $H_2O$ (20) was added and stirring continued for an additional 20 min. $NH_4OH$ (20 ml) was added and after stirring for 30 min the reaction mixture was evaporated. The residue was triturated with $H_2O$, filtered and the filtrate evaporated and purified by silica gel chromatography as per the procedure of Example 4 to yield the product as an off white solid (1.5 g). $^1$H NMR (DMSO-$d_6$) δ 1.1 [d, 6, CH(C$\underline{H}_3$)$_2$], 2.77 [m, 1, C$\underline{H}$(CH$_3$)$_2$], 3.33–3.6 (m, 5, OC$\underline{H}_3$, $\underline{H}$-5'), 3.93 (m, 1, $\underline{H}$-4'), 4.22 (m, 1), 4.3 (m, 1), 5.1 (t, 1, 5'-O$\underline{H}$), 5.28 (d, 1, 3'-O$\underline{H}$), 5.9 (d, 1, $\underline{H}$-1'), 8.28 (s, 1, $\underline{H}$-8) and 11.9 (br s, 1, N$\underline{H}$).

Example 37

N2-Isobutyryl-5'-dimethoxytrityl-2'-O-methylguanosine

N2-Isobutyryl-2'-O-methylguanosine (1.5 g) was treated with dimethoxytrityl chloride (1.5 g, 1.1 eq), and dimethylaminopyridine (100 mg as a catalyst) in pyridine (50 ml) as per the procedure of Example 5 to yield the product as a foam (2.6 g). $^1$H NMR (DMSO-$d_6$) δ 1.14 (d, 6, CH(C$\underline{H}_3$)$_2$], 2.75 [m, 1, C$\underline{H}$(CH$_3$)$_2$], 3.5 (m, 2, $\underline{H}$-5'), 3.74 (s, 6, OC$\underline{H}_3$), 4.05 (m, 1), 4.33 (m, 1), 5.26 (d, 1, 3'-O$\underline{H}$), 5.95 (d, 1, $\underline{H}$-1'), 6.83, 7.2, 7.35 (m, 13, DMTr), 8.15 (s, 1, $\underline{H}$-8), 11.6 (br s, 1, N$\underline{H}$) and 12.1 (br s, 1, N$\underline{H}$).

Example 38

N2-Isobutyryl-5'-dimethoxytrityl-2'-O-methylguanosine 3'-β-cyanoethyl-N,N-diisopropylphosphoramidate N2-Isobutyryl-5'-dimethoxytrityl-2'-O-methyl-guanosine (20 g) was treated with bis-(N,N-diisopropylamino)-2-cyanoethylphosphite (10.8 g) and N,N-diisopropylammonium tetrazolide (1.6 g) as per the procedure of Example 6 to yield the product (15.7 g). $^{31}$P NMR (CDCl$_3$) δ 148.97 and 147.96.

Example 39

N2,N6-Diisobutyryl-2,6-diamino-9-(2-O-methyl-β-D-ribo-furanosyl) Purine 2,6-diamino-9-(2-O-methyl-β-D-ribofuranosyl)purine (700 mg) in pyridine (20 ml) was treated with trimethylsilyl chloride (2.1 ml, 7 eq) and isobutyryl chloride (1.25 ml, 5 eq) as per the procedure of Example 4 to yield the product as a foam (900 mg) after silica gel chromatography.

Example 40

N2,N6-Diisobutyryl-2,6-diamino-9-(5-O-dimethoxytrityl-2-O-methyl-β-D-ribofuranosyl) purine N2,N6-Diisobutyryl-2,6-diamino-9-(2-O-methyl-β-D-ribofuranosyl)purine (900 mg) was treated with dimethoxytrityl chloride (1.0 g) and dimethylaminopyridine (20 mg as a catalyst) in pyridine (30 m) as per the procedure of Example 5 to yield the product as a foam (700 mg). $^1$H NMR (DMSO-$d_6$) δ 0.96–1.16 [m, 12, 2×CH(CH$_3$)$_2$], 2.9 and 3.05 [M, 2, 2×C$\underline{H}$(CH$_3$)$_2$], 3.18 and 3.37 (ABX, 2, $\underline{H}$-5'), 3.38 (s, 3, OC$\underline{H}_3$), 3.7 (s, 6, OC$\underline{H}_3$), 4.05 (m, 1, $\underline{H}$-4'), 4.44 (m, 2, $\underline{H}$-2', $\underline{H}$-3'), 5.24 (d, 1, 3'-O$\underline{H}$), 6.06 (d, 1, $\underline{H}$-1'), 6.78, 7.2, 7.33 (m, 13, Ar), 8.22 (s, 1, $\underline{H}$-8), 10.3 (br s, 1, N$\underline{H}$) and 10.57 (br s, 1, N$\underline{H}$).

Example 41

N2,N6-Diisobutyryl-2,6-diamino-9-(5-O-dimethoxytrityl-2-O-methyl-β-D-ribofuranosyl) purine 3'-β-Cyanoethyl-N,N-diisopropylphosphoramidate N2,N6-Diisobutyryl-2,6-diamino-9-(5-O-dimethoxytrityl-2-O-methyl-β-D-ribofuranosyl)purine (600 mg) was treated with bis-(N,N-diisopropylamino)-2-cyanoethylphosphite (500 µl) and N,N-diisopropylammonium tetrazolide (80 mg) overnight at RT. The reaction mixture was partitioned against dil. $Na_2CO_3$/CHCl$_2$ and then $Na_2CO_3$/NaCl and dried over MgSO$_4$. The organic layer was evaporated to a foam (500 mg). $^{31}$P NMR (CDCl$_3$) δ 151.1 (doublet).

Example 42

2,6-Diamino-9-(2-O-octadecyl-β-D-ribofuranosyl) purine 2,6-Diamino-9-(β-D-ribofuranosyl)purine (50 g, 180 mmol) and sodium hydride (7 g) in DMF (1 l) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/CH$_2$Cl$_2$. The product containing fraction were evaporated to yield the product (11 g). $^1$H NMR (DMSO-d$_6$) δ 0.84 (t, 3, CH$_2$); 1.22 [m, 32, O—CH$_2$—CH$_2$—(CH$_2$)$_{16}$—]; 1.86 (m, 2, O—CH$_2$CH$_2$—); 3.25 (m, 2, O—CH$_2$—); 3.93 (d, 1, 4'H); 4.25 (m, 1, 3'H); 4.38 (t, 1, 2'H); 5.08 (d, 1, 3'-OH); 5.48 (t, 1, 5'-OH); 5.75 (s, 2, 6-NH$_2$); 5.84 (d, 1, 1'-H); 6.8 (s, 2, 2-NH$_2$); and 7.95 (s, 1, 8-H).

Example 43

2'-O-Octadecylguanosine 2,6-Diamino-9-(2-O-octadecyl-β-D-ribofuranosyl)purine (10 g) in 0.1 M sodium phosphate buffer (50 ml, pH 7.4), 0.1 M tris buffer (1000 ml, pH 7.4) and DMSO (1000 ml) was treated with adenosine deaminase (1.5 g) as per the procedure of Example 3. At day 3, day 5 and day 7 an additional aliquot (500 mg, 880 mg and 200 mg, respectively) of adenosine deaminase was added. The reaction was stirred for a total of 9 day and after purification by silica gel chromatography yielded the product (2 g). An analytical sample was recrystallized from MeOH $^1$H NMR (DMSO-d$_6$) δ 0.84 (t, 3, CH$_3$), 1.22 [s, 32, O—CH$_2$—CH$_2$—(CH$_2$)$_{16}$], 5.07 (m, 2, 3'-OH5'-OH); 5.78 (d, 1, 1'-H); 6.43 (s, 2, NH$_2$), 7.97 (s, 1, 8-H) and 10.64 (s, 1, NH$_2$). Anal. Calcd. for C$_{28}$H$_{49}$N$_5$O$_5$: C, 62.80; H, 9.16; N, 12.95. Found: C, 62.54; H, 9.18; N, 12.95.

Example 44

N2-Isobutyryl-2'-O-octadecylguanosine

2'-O-Octadecylguanosine (1.9 g) in pyridine (150 ml) was treated with trimethylsilyl chloride (2 g, 5 eq) and isobutyryl chloride (2 g, 5 eq) as per the procedure of Example 4. The product was purified by silica gel chromatography (eluted with 3% MeOH/EtOAc) to yield 1.2 g of product. $^1$H NMR (DMSO-d$_6$) δ 0.85 [t, 3, CH$_3$], 1.15 [m, 38, O—CH$_2$CH$_2$(CH$_2$)$_{16}$, CH(CH$_3$)$_2$], 2.77 [m, 1, CH(CH$_3$)$_2$], 4.25 (m, 2, 2'H, 3'H); 5.08 (t, 1, 5'-OH), 5.12 (d, 1, 3'-OH), 5.87 (d, 1, 1'-H), 8.27 (s, 1, 8-H), 11.68 (s, 1, NH$_2$) and 12.08 (s, 1, NH$_2$). Anal. Calcd. for C$_{32}$H$_{55}$N$_5$O$_6$: C, 63.47; H, 9.09; N, 11.57. Found: C, 63.53; H, 9.20; N, 11.52.

Example 45

2,6-Diamino-9-[2-O-(imidazol-1-yl)butyl-β-D-ribofuranosyl]purine 2,6-Diamino-(9-β-D-ribofuranosyl)purine (5.0 g) in DMF (400 ml) was treated with sodium hydride (0.78 g). After stirring an additional 30 min a further portion of sodium hydride (2.6 g) was added immediately followed by bromobutylimidazole (9.9 g) in DMF (25 ml). The reaction mixture was stirred overnight and quenched with H$_2$O. The reaction mixture was filtered through celite and evaporated to yield an oily product. TLC showed a mixture of isomers.

Example 46

2'-O-(Imidazol-1-yl)butylguanosine

A mixture of the 2,6-diamino-9-[2-O-(imidazol-1-yl)butyl-β-D-ribofuranosyl]purine and 2, 6-diamino-9-[3-O-(imidazol-1-yl)butyl-β-D-ribofuranosyl]purine isomers in 0.1 M tris buffer (pH 7.4), 0.1 M NaSO$_4$ buffer (pH 7.4) and DMSO will treated with adenosine deaminase at RT for 5 days as per the procedure of Example 3. The product containing fractions will be purified by silica gel chromatography and the product containing fraction evaporated to give the product.

Example 47

N2-Isobutyryl-2'-O-(imidazol-1-yl)butylguanosine

2'-O-(imidazol-1-yl)butylguanosine in pyridine will be treated with trimethylsilyl chloride (5 eq) and isobutyryl chloride (5 eq) as per the procedure of Example 4 to yield the product.

Example 48

N2-Isobutyryl-5'-dimethoxytrityl-2'-O-(imidazol-1-yl)butyl-guanosine

N2-Isobutyryl-2'-O-(imidazol-1-yl)butylguanosine will be treated with dimethoxytrityl chloride (1.1 eq), and dimethylaminopyridine (as a catalyst) in pyridine as per the procedure of Example 5. After chromatography purification, the product containing fractions will be evaporated to yield the product).

Example 49

A. Evaluation of the Thermodynamics of Hybridization of 2'-modified Oligonucleotides The ability of the 2'-modified oligonucleotides to hybridize to their complementary RNA or DNA sequences is determined by thermal melting analysis. The RNA complement is synthesized from T7 RNA polymerase and a template-promoter of DNA synthesized with an Applied Biosystems, Inc. 380B RNA species was purified by ion exchange using FPLC (LKB Pharmacia,Inc.). Natural antisense oligonucleotides or those containing 2'-O-alkyl guanosine at specific locations are added to either the RNA or DNA complement at stoichiometric concentrations and the absorbance (260 nm) hyperchromicity upon duplex to random coil transition was monitored using a Gilford Response II spectrophotometer. These measurements are performed in a buffer of 10 mM Na-phosphate, pH 7.4, 0.1 mM EDTA, and NaCl to yield an ionic strength of 10 either 0.1 M or 1.0 M. Data is analyzed by a graphic representation of $1/T_m$ vs ln[Ct], where [Ct] was the total oligonucleotide concentration. From this analysis the thermodynamic parameters is determined. Based upon the information gained concerning the stability of the duplex of heteroduplex formed, the placement of 2'-O-alkyl guanosine into oligonucleotides are assessed for their effects on helix stability. Modifications that drastically alter the stability of the hybrid exhibit reductions in the free energy (delta G) and decisions concerning their usefulness as antisense oligonucleotides are made.

B. Fidelity of Hybridization of 2'-modified Oligonucleotides

The ability of the 2'-O-alkyl guanosine modified antisense oligo-nucleotides to hybridize with absolute specificity to the targeted mRNA is shown by Northern blot analysis of purified target mRNA in the presence of total cellular RNA. Target mRNA is synthesized from a vector containing the cDNA for the target mRNA located downstream from a T7 RNA polymerase promoter. Synthesized mRNA was electrophoresed in an agarose gel and transferred to a suitable support membrane (ie. nitrocellulose). The support membrane was blocked and probed using [$^{32}$P]-labeled antisense oligonucleotides. The stringency will be determined by replicate blots and washing in either elevated temperatures or decreased ionic strength of the wash buffer. Autoradiography was performed to assess the presence of heteroduplex formation and the autoradiogram quantitated by laser densitometry (LKB Pharmacia, Inc.). The specificity of hybrid formation was determined by isolation of total cellular RNA by standard techniques and its analysis by agarose electrophoresis, membrane transfer and probing with the labeled 2'-modified oligonucleotides. Stringency was predetermined for the unmodified antisense oligonucleotides and the conditions used such that only the specifically targeted mRNA was capable of forming a heteroduplex with the 2'-modified oligonucleotide.

Example 50

Nuclease Resistance

A. Evaluation of the Resistance of 2'-modified Oligonucleotides to Serum and Cytoplasmic Nucleases Natural phosphorothioate, and 2-modified oligonucleotides were assessed for their resistance to serum nucleases by incubation of the oligonucleotides in media containing various concentrations of fetal calf serum or adult human serum. Labeled oligonucleotides were incubated for various times, treated with protease K and then analyzed by gel electrophoresis on 20% polyacrylamine-urea denaturing gels and subsequent autoradiography. Autoradiograms were quantitated by laser densitometry. Based upon the location of the modifications and the known length of the oligonucleotide it was possible to determine the effect on nuclease degradation by the particular 2'-modification. For the cytoplasmic nucleases, a HL60 cell line was used. A post-mitochondrial supernatant was prepared by differential centrifugation and the labeled oligonucleotides were incubated in this supernatant for various times. Following the incubation, oligo-nucleotides were assessed for degradation as outlined above for serum nucleolytic degradation. Autoradiography results were quantitated for comparison of the unmodified, the phosphorothioates, and the 2'-modified oligonucleotides.

B. Evaluation of the Resistance of 2'-Modified Oligonucleotides to Specific Endo- and Exo-nucleases Evaluation of the resistance of natural and 2'-modified oligonucleotides to specific nucleases (ie, endonucleases, 3', 5'-exo-, and 5',3'-exonucleases) was done to determine the exact effect of the modifications on degradation. Modified oligonucleotides were incubated in defined reaction buffers specific for various selected nucleases. Following treatment of the products with proteinase K, urea was added and analysis on 20% polyacrylamide gels containing urea was done. Gel products were visualized by staining using Stains All (Sigma Chemical Co.). Laser densitometry was used to quantitate the extend of degradation. The effects of the 2'-modifications were determined for specific nucleases and compared with the results obtained from the serum and cytoplasmic systems.

What is claimed is:
1. A compound having the structure:

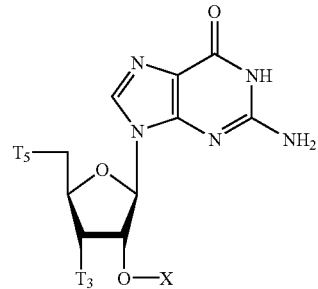

wherein
X is $R_1-(R_2)_n$;
$R_1$ is $C_2-C_{20}$ alkyl, $C_2-C_{20}$ alkenyl, or $C_2-C_{20}$ alkynyl and n is 1 to 6;
$R_2$ is halogen, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether; and
either one of $T_3$ and $T_5$ is OH, a hydroxyl blocking group, phosphate or an activated phosphate group and the other of $T_3$ and $T_5$ is a nucleotide or both $T_3$ and $T_5$ are nucleotides.
2. A compound having the structure:

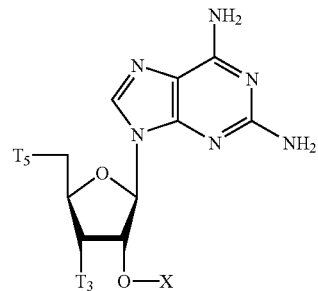

wherein
X is $R_1-(R_2)_n$;
$R_1$ is $C_1-C_{20}$ alkyl, $C_4-C_{20}$ alkenyl, or $C_2-C_{20}$ alkynyl;
$R_2$ is halogen, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
either one of $T_3$ and $T_5$ is OH, a hydroxyl blocking group, phosphate or an activated phosphate group and the other of $T_3$ and $T_5$ is a nucleotide, or both $T_3$ and $T_5$ are nucleotides; and
n is an integer from 1 to 6.
3. The compound of claim 1 wherein $R_1$ is $C_4-C_{20}$ alkyl.
4. The compound of claim 1 wherein $R_1$ is $C_5-C_{20}$ alkyl.

5. The compound of claim 1 wherein $R_1$ is $C_3$–$C_{20}$ alkyl and n is 1.

6. The compound of claim 1 wherein $R_1$ is $C_4$–$C_{20}$ alkenyl and n is 1.

7. The compound of claim 1 wherein $R_1$ is $C_2$–$C_{20}$ alkynyl and n is 1.

8. The compound of claim 1 wherein $R_1$ is $C_2$–$C_{20}$ alkyl and n is 1 to 6.

9. The compound of claim 1 wherein $R_1$ is $C_2$–$C_{20}$ alkenyl and n is 1 to 6.

10. The compound of claim 1 wherein $R_1$ is $C_2$–$C_{20}$ alkynyl and n is 1 to 6.

11. The compound of claim 2 wherein $R_1$ is $C_1$–$C_{20}$ alkyl.

12. The compound of claim 2 wherein $R_1$ is $C_4$–$C_{20}$ alkenyl.

13. The compound of claim 2 wherein $R_1$ is $C_2$–$C_{20}$ alkynyl.

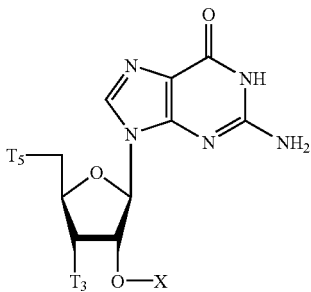

14. A compound having the structure:
wherein
X is $R_1$—$(R_2)_n$;
$R_1$ is $C_4$–$C_{20}$ alkyl, $C_4$–$C_{20}$ alkenyl, or $C_2$–$C_{20}$ alkynyl and n is 0; or $R_1$ is $C_1$–$C_{20}$ alkyl, $C_2$–$C_{20}$ alkenyl, or $C_2$–$C_{20}$ alkynyl and n is 1 to 6;

$R_2$ is hydroxyl, thiol, keto, carboxyl, or amino; and either one of $T_3$ and $T_5$ is OH, a hydroxyl blocking group, phosphate or an activated phosphate group and the other of $T_3$ and $T_5$ is a nucleotide or both $T_3$ and $T_5$ are nucleotides.

15. A compound having the structure:

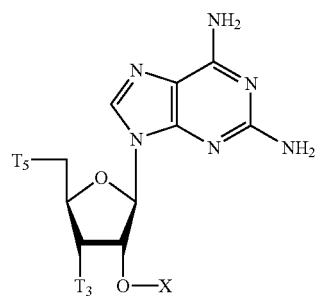

wherein

X is $R_1$—$(R_2)_n$;

$R_1$ is $C_1$–$C_{20}$ alkyl, $C_4$–$C_{20}$ alkenyl, or $C_2$–$C_{20}$ alkynyl;

$R_2$ is hydroxyl, thiol, keto, carboxyl, or amino;

either one of $T_3$ and $T_5$ is OH, a hydroxyl blocking group, phosphate or an activated phosphate group and the other of $T_3$ and $T_5$ is a nucleotide, or both $T_3$ and $T_5$ are nucleotides; and n is an integer from 0 to 6.

* * * * *

UNITED STATES PATENT AND TRADEMARK OFFICE
CERTIFICATE OF CORRECTION

| | |
|---|---|
| PATENT NO. | : 7,101,993 B1 |
| APPLICATION NO. | : 07/967267 |
| DATED | : September 5, 2006 |
| INVENTOR(S) | : Phillip Dan Cook |

It is certified that error appears in the above-identified patent and that said Letters Patent is hereby corrected as shown below:

Title Page
1) Title Page:
Item [63], Related U.S. Application Data, please delete "Continuation-in-part of application No. 07/918,362, filed on Jul. 23, 1992, now Pat. No. 5,506,351, which is a continuation-in-part of application No. 07/463,358, filed on Jan. 11, 1990, now abandoned, which is a continuation-in-part of application No. 07/566,977, filed on Aug. 13, 1990, now abandoned"

and insert therefore

--Continuation-in-part of application No. 07/918,362, filed on Jul. 23, 1992, now Pat. No. 5,506,351, and application No. PCT/US91/00243, filed on Jan. 11, 1991, which is a continuation-in-part of application No. 07/566,977, filed on Aug. 13, 1990, now abandoned, and application No. 07/463,358, filed on Jan. 11, 1990, now abandoned--;

Title Page
2) Page 2, OTHER PUBLICATION, "Robins" reference, please delete "2-aminoaldenosine" and insert therefore --2-aminoadenosine--;

3) Column 1, line 8, please insert --and Ser. No. US91/00243 filed on Jan, 11, 1991-- between "5,506,351" and "which";

4) Column 2, line 19, please delete "2-O-alkylated" and insert therefore --2'-O-alkylated--;

5) Column 5, line 22, please delete ".";

6) Column 9, line 5, please delete "$NH_Z$" and insert therefore --$NH_2$--;

7) Column 9, line 5, please delete "($2NH_Z$" and insert therefore --($2NH_2$--;

8) Column 9, line 8, please delete "N,N-diisopropylaminochlorophosphine" and insert therefore --N,N-diisopropyl aminochlorophosphine--;

9) Column 11, line 1, please delete "similarly" and insert therefore --Similarly--;

10) Column 13, line 44, please delete "$C_{13}H_{20}N_6O_4 \cdot \frac{1}{2}H_2O$: " and insert therefore --$C_{13}H_{20}N_6O_4 \cdot \frac{1}{2}H_2O$:--;

11) Column 13, line 47, please delete "B";

UNITED STATES PATENT AND TRADEMARK OFFICE
CERTIFICATE OF CORRECTION

PATENT NO. : 7,101,993 B1
APPLICATION NO. : 07/967267
DATED : September 5, 2006
INVENTOR(S) : Phillip Dan Cook It is certified that error appears in the above-identified patent and that said Letters Patent is hereby corrected as shown below:

12) Column 14, line 6, please delete "O-CH$_2$)" and insert therefore --O-C$\underline{H}_2$)--;

13) Column 14, line 34, please delete "C$_{17}$H$_{25}$N$_5$O$_6$.½H$_2$O: " and insert therefore --C$_{17}$H$_{25}$N$_5$O$_6$·½H$_2$O:--;

14) Column 14, line 48, please delete "CH$_2$CI$_2$/2xdil" and insert therefore --CH$_2$Cl$_2$/2x dil--;

15) Column 14, line 57, please delete "C$_{38}$H$_{42}$N$_5$O$_8$.H$_2$O: " and insert therefore --C$_{38}$H$_{42}$N$_5$O$_8$·H$_2$O:--;

16) Column 16, line 26, please delete "C$_{40}$H$_{47}$N$_5$O$_8$.½H$_2$O: " and insert therefore --C$_{40}$H$_{47}$N$_5$O$_8$·½H$_2$O:--;

17) Column 17, line 12, please delete "3'-O$\underline{H}$5'-O$\underline{H}$" and insert therefore --3'-O$\underline{H}$ 5'-O$\underline{H}$--;

18) Column 17, line 30, please delete "C2" and insert therefore --C$_2$--;

19) Column 18, line 9, please delete "$^1$ H" and insert therefore --$^1$H--;

20) Column 18, line 20, please delete "D-ribo-furanosyl" and insert therefore --D-ribofuranosyl--;

21) Column 19, line 57, please delete "3'-OH)" and insert therefore --3'-O$\underline{H}$)--;

22) Column 19, line 59, please delete "C$_{21}$H$_{22}$N$_6$O$_7$.½H$_2$O: " and insert therefore --C$_{21}$H$_{22}$N$_6$O$_7$·½H$_2$O:--;

23) Column 20, line 9, please delete "C$_{25}$H$_{28}$N$_6$O$_8$.½H$_2$O: " and insert therefore --C$_{25}$H$_{28}$N$_6$O$_8$·½H$_2$O:--;

24) Column 20, line 15, please delete "phthalimido)propylquanosine" and insert therefore --phthalimido)propylguanosine--;

25) Column 20, line 29, please delete "C$_{46}$H$_{46}$N$_6$O$_{10}$.H$_2$O:" and insert therefore --C$_{46}$H$_{46}$N$_6$O$_{10}$·H$_2$O:--;

26) Column 20, line 45, please delete "N2-Dimethylaminomethylidene-5=-" and insert therefore --N2-Dimethylaminomethylidene-5'- --;

UNITED STATES PATENT AND TRADEMARK OFFICE
CERTIFICATE OF CORRECTION

PATENT NO. : 7,101,993 B1
APPLICATION NO. : 07/967267
DATED : September 5, 2006
INVENTOR(S) : Phillip Dan Cook It is certified that error appears in the above-identified patent and that said Letters Patent is hereby corrected as shown below:

27) Column 20, line 53, please delete "1xwith" and insert therefore --1x with--;

28) Column 20, line 65, please delete "$C_{45}H_{45}N_7O_9.\frac{1}{2}H_2O:$ " and insert therefore --$C_{45}H_{45}N_7O_9 \cdot \frac{1}{2}H_2O$:--;

29) Column 21, line 60, please delete "$C_{23}H_{26}N_6O_7.\frac{1}{2}H_2O:$ " and insert therefore --$C_{23}H_{26}N_6O_7 \cdot \frac{1}{2}H_2O$:--;

30) Column 22, line 3, please delete "2xwith" and insert therefore --2x with--;

31) Column 22, line 11, please delete "$C_{27}H_{32}N_6O_8.\frac{1}{2}H_2O:$ " and insert therefore --$C_{27}H_{32}N_6O_8 \cdot \frac{1}{2}H_2O$:--;

32) Column 22, line 31, please delete "$C_{48}H_5ON_6O_{10}.\frac{1}{2}H_2O:$ " and insert therefore --$C_{48}H_{50}N_6O_{10} \cdot \frac{1}{2}H_2O$:--;

33) Column 22, line 39, please delete "2,6-diamino-9-(□-D-ribo-furanosyl)" and insert therefore --2,6-diamino-9-(□-D-ribofuranosyl)--;

34) Column 22, line 48, please delete "$C_{22}H_{40}N_6O_5Si_2\frac{1}{2}H_2O:$ " and insert therefore --$C_{22}H_{40}N_6O_5Si_2 \cdot \frac{1}{2}H_2O$:--;

35) Column 23, line 16, please delete "$C_{11}H_{16}N_6O_4.\frac{1}{2}H_2O:$ " and insert therefore --$C_{11}H_{16}N_6O_4 \cdot \frac{1}{2}H_2O$: --;

36) Column 23, line 34, please delete "$C_{11}H_{15}N_5O_5.\frac{1}{2}H_2O:$ " and insert therefore --$C_{11}N_{15}N_5O_5 \cdot \frac{1}{2}H_2O$:--;

37) Column 23, line 50, please delete "C<u>H</u>(C<u>H</u>$_3$)$_2$]" and insert therefore -- C<u>H</u>(CH$_3$)$_2$]--;

38) Column 24, line 6, please delete "N2-Isobutyryl-5'-dimethyoxytrityl-2'-O-methyl-guanosine" and insert therefore --N2-Isobutyry1-5'-dimethoxytrityl-2'-O-methylguanosine--;

39) Column 24, line 16, please delete "D-ribo-furanosyl) " and insert therefore --D-ribofuranosyl)--;

40) Column 25, line 24, please delete "3'-O<u>H</u>5'-O<u>H</u>) " and insert therefore --3'-O<u>H</u> 5'-O<u>H</u>--;

41) Column 25, line 39, please delete "C<u>H</u>(C<u>H</u>$_3$)$_2$] " and insert therefore --C<u>H</u>(CH$_3$)$_2$]--;

UNITED STATES PATENT AND TRADEMARK OFFICE
CERTIFICATE OF CORRECTION

PATENT NO. : 7,101,993 B1
APPLICATION NO. : 07/967267
DATED : September 5, 2006
INVENTOR(S) : Phillip Dan Cook It is certified that error appears in the above-identified patent and that said Letters Patent is hereby corrected as shown below:

42) Column 25, line 62, please delete "2, 6-diamino-9-[3-O-" and insert therefore --2,6-diamino-9-[3-O- --;

43) Column 29, Claim 10, please insert --1-- between "claim" and "wherein";

44) Column 29, lines 17-27, please delete " 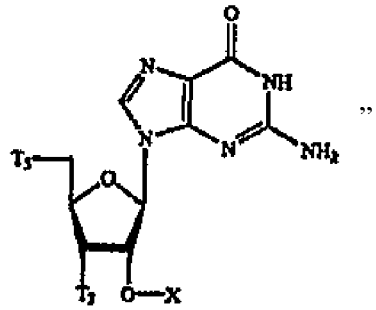 "

45) Column 29, claim 14, please insert -- 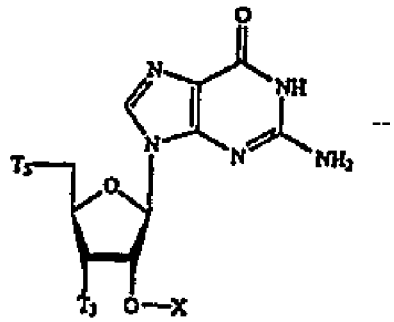 -- between "structure: " and "wherein".

Signed and Sealed this

Nineteenth Day of December, 2006

JON W. DUDAS
*Director of the United States Patent and Trademark Office*